(12) United States Patent
Burroughs et al.

(10) Patent No.: US 10,315,198 B2
(45) Date of Patent: Jun. 11, 2019

(54) CLAMP FOR FAST PCR HEATING

(71) Applicant: BJS IP Ltd, Middlesex (GB)

(72) Inventors: Nicholas Burroughs, Bath (GB); Ian Gunter, Berkshire (GB); Richard Lewis, Middlesex (GB)

(73) Assignee: BJS IP LTD, Middlesex (GB)

( * ) Notice: Subject to any disclaimer, the term of this patent is extended or adjusted under 35 U.S.C. 154(b) by 205 days.

(21) Appl. No.: 15/408,313

(22) Filed: Jan. 17, 2017

(65) Prior Publication Data
US 2017/0189911 A1    Jul. 6, 2017

Related U.S. Application Data

(62) Division of application No. 14/402,628, filed as application No. PCT/GB2013/051353 on May 23, 2013, now Pat. No. 9,579,657.
(Continued)

(51) Int. Cl.
*B01L 7/00* (2006.01)
*B01L 3/00* (2006.01)
(Continued)

(52) U.S. Cl.
CPC ............ *B01L 7/52* (2013.01); *B01L 3/50851* (2013.01); *B01L 9/50* (2013.01); *C12Q 1/686* (2013.01);
(Continued)

(58) Field of Classification Search
CPC .......... B01L 3/50851; B01L 7/52; B01L 9/50; B01L 2200/02; B01L 2300/0829; B01L 2300/1827
(Continued)

(56) References Cited

U.S. PATENT DOCUMENTS 2,815,777 A    12/1957  Arvids et al.
5,455,175 A    10/1995  Wittwer et al.
(Continued)

FOREIGN PATENT DOCUMENTS

AU    2011342975 B2    4/2015
CN       1427744 A     7/2003
(Continued)

OTHER PUBLICATIONS

Office action dated Jun. 29, 2017 for U.S. Appl. No. 15/211,625.
(Continued)

*Primary Examiner* — Michael L Hobbs
(74) *Attorney, Agent, or Firm* — Wilson Sonsini Goodrich & Rosati

(57) ABSTRACT

This disclosure provides a thermocycler system for performing polymerase chain reaction. The thermocycler system can comprise a plurality of bus bars, a microplate, a clamp and a current application device in electrical communication with the bus bars. The clamp is suitable for forming a low resistance electrical connection between the microplate and an individual bus bar of the plurality of bus bars. In some instances, the clamp includes a spring-loaded pivot and a ram. Operation of the clamp forces the microplate into contact with the bus bar, or vice versa, to provide an electrical contact between the microplate and the bus bar. The microplate can comprise a substrate having a metallic material for heating samples, and a barrier layer disposed adjacent to the substrate.

20 Claims, 18 Drawing Sheets

Related U.S. Application Data

(60) Provisional application No. 61/651,425, filed on May 24, 2012.

(51) Int. Cl.
*B01L 9/00* (2006.01)
*C12Q 1/686* (2018.01)

(52) U.S. Cl.
CPC ....... B01L 2200/02 (2013.01); B01L 2200/12 (2013.01); B01L 2300/0654 (2013.01); B01L 2300/0829 (2013.01); B01L 2300/0887 (2013.01); B01L 2300/1822 (2013.01); B01L 2300/1827 (2013.01)

(58) Field of Classification Search
USPC ...................................................... 435/303.1
See application file for complete search history.

(56) References Cited

U.S. PATENT DOCUMENTS

| | | | |
|---|---|---|---|
| 5,475,610 A | 12/1995 | Atwood et al. | |
| 5,525,300 A | 6/1996 | Danssaert et al. | |
| 5,656,493 A | 8/1997 | Mullis et al. | |
| 5,779,981 A | 7/1998 | Danssaert et al. | |
| 5,856,174 A | 1/1999 | Lipshutz et al. | |
| 5,960,976 A | 10/1999 | Tsuno | |
| 5,965,410 A | 10/1999 | Chow et al. | |
| 6,054,263 A | 4/2000 | Danssaert et al. | |
| 6,140,613 A | 10/2000 | Tsuno | |
| 6,312,886 B1 | 11/2001 | Lee et al. | |
| 6,436,355 B1 | 8/2002 | Lee et al. | |
| 6,533,255 B1 | 3/2003 | Mitsuhashi et al. | |
| 6,635,492 B2 | 10/2003 | Gunter | |
| 6,703,236 B2 | 3/2004 | Atwood et al. | |
| 6,730,883 B2* | 5/2004 | Brown ................ B01L 3/50851 219/385 | |
| 6,750,661 B2 | 6/2004 | Brooks et al. | |
| 6,787,338 B2 | 9/2004 | Wittwer et al. | |
| 6,833,536 B2 | 12/2004 | Shigeura | |
| 6,878,905 B2 | 4/2005 | Brown et al. | |
| 6,949,725 B2* | 9/2005 | Gunter ................ B01L 3/50851 219/477 | |
| 6,962,821 B2 | 11/2005 | Danssaert et al. | |
| 6,967,489 B2 | 11/2005 | Brooks et al. | |
| 7,081,600 B2 | 7/2006 | Brown et al. | |
| 7,122,799 B2 | 10/2006 | Hsieh et al. | |
| 7,173,218 B2 | 2/2007 | Shigeura et al. | |
| 7,238,321 B2 | 7/2007 | Wittwer et al. | |
| 7,264,950 B1 | 9/2007 | Lee et al. | |
| 7,287,181 B2 | 10/2007 | Thompson | |
| 7,294,812 B2 | 11/2007 | Shigeura et al. | |
| 7,311,794 B2 | 12/2007 | Joseph et al. | |
| 7,429,479 B2* | 9/2008 | Harding ................ B01L 3/5027 356/246 | |
| 7,460,223 B2 | 12/2008 | Harding | |
| 7,488,595 B2 | 2/2009 | Hwang et al. | |
| 7,622,296 B2 | 11/2009 | Joseph et al. | |
| 7,628,961 B2 | 12/2009 | Hwang et al. | |
| 7,659,096 B2 | 2/2010 | Lee et al. | |
| 7,674,431 B2 | 3/2010 | Ganesan | |
| 7,704,735 B2 | 4/2010 | Facer et al. | |
| 7,767,439 B2 | 8/2010 | Oh et al. | |
| 7,767,447 B2 | 8/2010 | Breidenthal et al. | |
| 7,771,933 B2 | 8/2010 | Arciniegas et al. | |
| 7,799,557 B2 | 9/2010 | Oh et al. | |
| 7,829,025 B2 | 11/2010 | Ganesan et al. | |
| 7,833,709 B2 | 11/2010 | Joseph et al. | |
| 7,867,763 B2 | 1/2011 | Facer et al. | |
| 9,168,530 B2 | 10/2015 | Gunter et al. | |
| 9,579,657 B2 | 2/2017 | Burroughs et al. | |
| 2001/0019704 A1 | 9/2001 | Gunter | |
| 2005/0158725 A1 | 7/2005 | Yukimasa et al. | |
| 2006/0030037 A1 | 2/2006 | Joseph et al. | |
| 2007/0172395 A1 | 7/2007 | Lim et al. | |
| 2008/0095679 A1 | 4/2008 | John et al. | |
| 2008/0219894 A1 | 9/2008 | Ganesan et al. | |
| 2009/0325278 A1 | 12/2009 | Lee et al. | |
| 2010/0009335 A1* | 1/2010 | Joseph ................... C12M 23/12 435/3 | |
| 2010/0152066 A1 | 6/2010 | Malik et al. | |
| 2010/0158754 A1 | 6/2010 | Ganesan | |
| 2010/0297707 A1 | 11/2010 | Lee et al. | |
| 2010/0311070 A1 | 12/2010 | Oh et al. | |
| 2011/0152108 A1 | 6/2011 | Brenan et al. | |
| 2012/0214207 A1* | 8/2012 | Gunter ................ B01L 3/50851 435/91.2 | |
| 2014/0302562 A1 | 10/2014 | Burroughs | |
| 2015/0182969 A1 | 7/2015 | Burroughs | |
| 2015/0307910 A1 | 10/2015 | Gunter et al. | |
| 2016/0319331 A1 | 11/2016 | Burroughs | |

FOREIGN PATENT DOCUMENTS

| | | |
|---|---|---|
| CN | 1812839 A | 8/2006 |
| CN | 101065498 A | 10/2007 |
| CN | 101155641 A | 4/2008 |
| EP | 2651560 A1 | 10/2013 |
| EP | 2855019 A1 | 4/2015 |
| WO | WO-9511294 A1 | 4/1995 |
| WO | WO-9726993 A1 | 7/1997 |
| WO | WO-9824548 A1 | 6/1998 |
| WO | WO-0069561 A1 | 11/2000 |
| WO | WO-0123093 A1 | 4/2001 |
| WO | WO-0166254 A1 | 9/2001 |
| WO | WO-0172424 A1 | 10/2001 |
| WO | WO-03022439 A2 | 3/2003 |
| WO | WO-03024599 A1 | 3/2003 |
| WO | WO-03025226 A1 | 3/2003 |
| WO | WO-03022439 A3 | 5/2003 |
| WO | WO-03038127 A1 | 5/2003 |
| WO | WO-03042677 A1 | 5/2003 |
| WO | WO-03087410 A1 | 10/2003 |
| WO | WO-03104783 A1 | 12/2003 |
| WO | WO-2004031342 A1 | 4/2004 |
| WO | WO-2004108287 A1 | 12/2004 |
| WO | WO-2005058501 A1 | 6/2005 |
| WO | WO-2005118773 A2 | 12/2005 |
| WO | WO-2005118773 A3 | 2/2006 |
| WO | WO-2006035497 A1 | 4/2006 |
| WO | WO-2006053770 A1 | 5/2006 |
| WO | WO-2006105919 A1 | 10/2006 |
| WO | WO-2008157801 A2 | 12/2008 |
| WO | WO-2009002447 A1 | 12/2008 |
| WO | WO-2009111696 A1 | 9/2009 |
| WO | WO-2008157801 A3 | 9/2011 |
| WO | WO-2012080746 A1 | 6/2012 |
| WO | WO-2013175218 A1 | 11/2013 |
| WO | WO-2014140596 A1 | 9/2014 |

OTHER PUBLICATIONS

Office action dated Jul. 7, 2017 for U.S. Appl. No. 14/207,297.
AU2011342975 Examiner's Report No. 1, dated Sep. 11, 2014.
"Chinese Patent Application No. 201180064525.6 Second Office Action dated Oct. 10, 2015".
CN 201180064525.6 Office Action dated Feb. 12, 2015.
Co-pending U.S. Appl. No. 15/211,625, filed Jul. 15, 2016.
Dictionary of Physics, Baifukan Co., Ltd., (1984), p. 2324.
"Eurasian Office Action dated Mar. 2, 2015 for Application No. EA 201390892."
Eurasian Office Action dated Aug. 19, 2015 for Application No. EA 201390892.
International preliminary report on patentability with written opinion dated Sep. 24, 1015 for PCTGB2014-050769.
International search report and written opinion dated May 14, 2012 for PCT/GB2011/052497.
International search report and written opinion dated Aug. 13, 2013 for PCT/GB2013/051353.
International search report dated Jun. 10, 2014 for PCT/GB2014/050769.

(56) References Cited

OTHER PUBLICATIONS

"Japanese Patent Application No. 2013-543884 Office Action dated Oct. 5, 2015".
"Notice of allowance dated May 4, 2015 for U.S. Appl. No. 13/329,183."
"Notice of allowance dated Sep. 29, 2015 for U.S. Appl. No. 13/329,183."
Notice of allowance dated Oct. 14, 2016 for U.S. Appl. No. 14/402,628.
Office action dated Jan. 3, 2017 for U.S. Appl. No. 15/211,625.
Office action dated Jan. 12, 2017 for U.S. Appl. No. 14/207,297.
Office action dated Feb. 22, 2016 for U.S. Appl. No. 14/402,628.
Pal, D. et al. A portable battery-operated chip thermocycler based on induction heating. 2012. Sensors and Actuators A: Physical, 102(1), 151-156.
PCT/GB2011/052497 International Preliminary Report on Patentability dated Jun. 18, 2013.
PCT/GB2013/051353 International Preliminary Report on Patentability dated Dec. 4, 2014.
U.S. Appl. No. 14/792345, filed Jul. 6, 2015.
"U.S. Appl. No. 14/402,629 Restriction Requirement dated Nov. 25, 2015".
U.S. Appl. No. 13/329183 Office Action dated Jan. 7, 2015.
Zhang C et al: "PCR microfluidic devices for DNA amplification", Biotechnology Advances, 24 (3) ;2006, 243-284.
Kempitiya, et al. Localized microwave heating in microwells for parallel DNA amplification applications. Appl. Phys. Lett.94, 064106 (2009).
U.S. Appl. No. 14/792,345 Office action dated Sep. 5, 2017.
U.S. Appl. No. 15/211,625 Office action dated Nov. 22, 2017.
U.S. Appl. No. 14/207,297 Office Action dated Sep. 21, 2018.
European Serial No. 13726015.4 Office Action dated Mar. 13, 2019.

\* cited by examiner

CLAMP FOR FAST PCR HEATING

CROSS-REFERENCE

This application is a divisional of U.S. application Ser. No. 14/402,628, filed Nov. 20, 2014, now U.S. Pat. No. 9,579,657, which is a National Stage Entry of International Application No. PCT/GB2013/051353, filed May 23, 2013, which claims the benefit of U.S. Provisional Patent Application No. 61/651,425, filed May 24, 2012, each of which is entirely incorporated herein by reference.

BACKGROUND

In many fields, specimen carriers in the form of support sheets, which may have a multiplicity of wells or impressed sample sites, are used for various processes where small samples are heated or thermally cycled. A particular example is the Polymerase Chain Reaction method (often referred to as PCR) for replicating DNA samples. Such samples require rapid and accurate thermal cycling, and are typically placed in a multi-well block and cycled between several selected temperatures in a pre-set repeated cycle. It is important that the temperature of the whole of the sheet or more particularly the temperature in each well be as uniform as possible.

The samples may be liquid solutions, typically between 1 micro-1 and 200 micro-1 in volume, contained within individual sample tubes or arrays of sample tubes that may be part of a monolithic plate. The temperature differentials that may be measured within a liquid sample increase with increasing rate of change of temperature and may limit the maximum rate of change of temperature that may be practically employed.

Previous methods of heating such specimen carriers have involved the use of attached heating devices or the use of indirect methods where separately heated fluids are directed into or around the carrier.

The previous methods of heating suffer from the disadvantage that heat is generated in a heater that is separate from the specimen carrier that is required to be heated. Such heating systems and methods suffer from heat losses accompanying the transfer of heat from the heater to a carrier sheet of the specimen carrier. In addition, the separation of the heater from the specimen carrier introduces a time delay or "lag" in the temperature control loop. Thus, the application of power to the heating elements does not produce an instantaneous or near instantaneous increase in the temperature of the block. The presence of a thermal gap or barrier between the heater and the block requires the heater to be hotter than the block if heat energy is to be transferred from the heater to the block. Therefore, there is a further difficulty that cessation of power application to the heater does not instantaneously stop the block from increasing in temperature.

The lag in the temperature control loop will increase as the rate of temperature change of the block is increased. This may lead to inaccuracies in temperature control and limit the practical rates of change of temperature that may be used. Inaccuracies in terms of thermal uniformity and further lag may be produced when attached heating elements are used, as the elements are attached at particular locations on the block and the heat produced by the elements must be conducted from those particular locations to the bulk of the block. For heat transfer to occur from one part of the block to another, the first part of the block must be hotter than the other. Another problem with attaching a thermal element, particularly current Peltier effect devices, is that the interface between the block and the thermal device will be subject to mechanical stresses due to differences in the thermal expansion coefficients of the materials involved. Thermal cycling will lead to cyclic stresses that will tend to compromise the reliability of the thermal element and the integrity of the thermal interface.

SUMMARY

An aspect of the present disclosure provides a microplate for polymerase chain reaction ("PCR"), comprising a substrate comprising a metallic material for heating PCR samples and a barrier layer disposed adjacent to the substrate, the barrier layer formed of a first polymeric material. The microplate includes one or more wells for holding PCR samples, the one or more wells formed of a second polymeric material sealed to the barrier layer.

Another aspect of the present disclosure provides a clamp suitable for forming a low resistance electrical connection between a microplate and a bus-bar in a thermocycler, wherein the clamp comprises a spring-loaded pivot and a ram, wherein operation of the clamp forces the microplate into contact with the bus-bar.

Another aspect of the present disclosure provides a clamp configured to provide a low resistance electrical connection between a microplate and a bus-bar of a thermocycler, comprising (a) a handle coupled to a spring-loaded pivot, and (b) a ram coupled to the spring-loaded pivot point. The ram provides a clamp force of at least about 500 Newtons upon movement of the handle. Movement of the handle forces the microplate into contact with the bus-bar.

Another aspect of the present disclosure provides a method for forming a low resistance electrical connection between a microplate and a bus-bar in a thermocycler, wherein the method comprises clamping the microplate to the bus-bar with a clamp comprising a spring-loaded pivot and a ram.

Another aspect of the present disclosure provides a method for forming a low resistance electrical connection between a microplate and a bus-bar in a thermocycler, comprising (a) providing a clamp comprising a spring-loaded pivot coupled to a ram, and (b) using the spring-loaded pivot to provide linear motion to the ram to press the microplate against the bus-bar.

In some embodiments, the clamp is an over center toggle type clamp.

In some embodiments, the clamp provides control over the force applied by the ram over a range of adjustments.

In some embodiments, the clamp is adjusted such that the clamp can be closed by hand and the clamp is capable of forming a low resistance electrical connection between the microplate and the bus-bar.

In some embodiments, the clamp is capable of exerting a force of between about 1,500 and 2,000 Newtons.

In some embodiments, the clamp is capable of deforming the microplate, thereby disrupting an oxide film on the surface of the microplate.

In some embodiments, the electrical resistance at the interface of the microplate and the bus-bar is less than the resistance of the microplate.

In some embodiments, the microplate is consumable.

In some embodiments, the microplate comprises: (a) a substrate comprising a metallic material for heating a sample during PCR; (b) a barrier layer disposed adjacent to the substrate, the barrier layer formed of a first polymeric material; and (c) one or more wells for holding the sample during PCR, the one or more wells formed of a second polymeric material sealed to the barrier layer, wherein the substrate provides a PCR ramp rate of at least 5° C./second.

In some embodiments, the microplate is configured to heat samples upon the flow of electric current through the substrate.

In some embodiments, the metallic material has a resistivity between about $2\times10^{-8}$ ohm-m and $8\times10^{-8}$ ohm-m.

In some embodiments, the metallic material comprises aluminum.

In some embodiments, the microplate has a thickness of less than 1 mm.

Another aspect of the present disclosure provides a thermocycler comprising the clamp described herein.

Another aspect of the present disclosure provides a system for performing polymerase chain reaction (PCR), comprising: (a) a plurality of bus bars for electrically mating with a microplate; (b) a microplate, the microplate comprising a metallic material for heating a sample during PCR; (c) a clamp, the clamp comprising a spring-loaded pivot and a ram, wherein the clamp is capable of forcing the microplate in electrical communication with and removable from the bus bars; and (d) a current application device for applying current to the microplate.

Another aspect of the present disclosure provides a system for performing polymerase chain reaction (PCR), comprising: (a) a plurality of bus bars; (b) a microplate comprising a metallic material for heating a sample during PCR, wherein the microplate comprises electrodes, wherein an individual electrode of said microplate is configured to mate with an individual bus bar of said plurality of bus bars; (c) a clamp comprising a spring-loaded pivot coupled to a ram, wherein the clamp is capable of forcing the individual electrode of the microplate in electrical contact with said individual bus bar; and (d) a current application device in electrical communication with said bus bars, wherein said current application device is for applying current to said microplate.

In some embodiments, the microplate is in ohmic contact with the plurality of bus bars.

In some embodiments, the microplate comprises finger-like projections in electrical communication with the bus bars.

In some embodiments, the finger-like projections have surfaces comprising crinkles.

In some embodiments, the system further comprises an infrared sensor for measuring the temperature of the microplate.

In some embodiments, the system further comprises a plurality of temperature sensors for measuring the temperature of the microplate in a plurality of thermal zones.

In some embodiments, the plurality of temperature sensors provide continuous temperature measurements.

In some embodiments, temperature variation across the microplate is less than 0.5° C.

In some embodiments, the microplate comprises (a) a substrate comprising said metallic material for heating a sample during polymerase chain reaction (PCR); (b) a barrier layer disposed adjacent to the substrate, the barrier layer formed of a first polymeric material; and (c) one or more wells for holding said sample during PCR, the one or more formed of a second polymeric material sealed to the barrier layer. The substrate provides a PCR ramp rate of at least 5° C./second.

In some embodiments, the substrate provides a PCR ramp rate of at least 5° C./second ("s"). In an embodiment, the PCR ramp rate (or heating rate) is at least about 10° C./second. In another embodiment, the microplate is configured to heat samples upon the flow of electric current through the substrate. In another embodiment, the substrate is configured to be separated from PCR samples by 10 micrometers or less. In another embodiment, the second polymeric material is heat-sealed to the barrier layer. In another embodiment, the first polymeric material is chemically compatible with the second polymeric material. In another embodiment, the metallic material comprises aluminum or an aluminum alloy. In another embodiment, the substrate is for generating heat upon the flow of electrical current through the substrate. In another embodiment, the substrate is for increasing the temperature of a sample in the one or more wells at a rate between about 5° C./s and 15° C./s. In another embodiment, the metallic material has a resistivity between about $2\times10^{-8}$ ohm-m and $8\times10^{-8}$ ohm-m. In another embodiment, the one or more wells comprise at least 24 wells. In another embodiment, the one or more wells comprise at least 96 wells.

Another aspect of the present disclosure provides a microplate for PCR, comprising a substrate comprising a metallic material for heating PCR samples, and a coating layer disposed adjacent to the substrate, the coating layer formed of a first polymeric material. The microplate includes one or more wells formed of a second polymeric material sealed to the coating layer for containing PCR samples. The metal substrate provides well-to-well thermal uniformity of +/−2° C., +/−1° C., +/−0.5° C., +/−0.2° C., +/−0.1° C., +/−0.05° C. or better without an external heating element or a Peltier heating block.

Another aspect of the present disclosure provides a microplate for PCR, comprising a substrate comprising a metallic material for heating PCR samples, and a coating layer disposed adjacent to the substrate, the coating layer formed of a first polymeric material. The microplate includes one or more wells for containing PCR samples, the one or more wells formed of a second polymeric material sealed to the coating layer. The substrate provides a heating efficiency sufficient to allow for at least about 1 PCR cycle per minute, including fluorescence measurement for every cycle. In an embodiment, the substrate provides a heating efficiency sufficient to allow for at least about 0.1, 1, 2, 3, 4, 5, 6, 7, 8, 9, 10, 20, 30, 40, 50, 60, 70, 80, 90, 100, 200, 300, 400, 500, 1000 or more PCR cycles per minute. In another embodiment, the substrate comprises an aluminum alloy. In another embodiment, the substrate comprises aluminum. In another embodiment, the microplate has a thickness of less than about 1 millimeter ("mm"). In another embodiment, the microplate has a thickness of less than about 0.5 mm. In another embodiment, the coating layer (or barrier layer) has a thickness of less than about 10 micrometers ("microns"). In another embodiment, the microplate further comprises a layer of an infrared radiation-normalizing layer at a side of the substrate opposite the coating layer. In another embodiment, the radiation-normalizing layer has a thickness of less than 5 microns. In another embodiment, the barrier layer has a thickness of less than 10 micrometers.

Another aspect of the present disclosure provides a disposable sample holder for use with PCR, comprising an aluminum substrate coated with a first polymeric material and a plurality of wells heat-sealed to the first polymeric material, the plurality of wells formed of a second polymeric material compatible with the first polymeric material.

Another aspect of the present disclosure provides a disposable sample holder for use with PCR having an aluminum-containing substrate for providing heat to a plurality of wells of the disposable sample holder, the disposable sample holder having a weight less than or equal to about 30 g. In an embodiment, the disposable sample holder has a weight less than or equal to about 20 g. In another embodiment, the disposable sample holder has a weight less than or equal to about 15 g. In another embodiment, the disposable sample holder has a weight less than or equal to about 10 g. In another embodiment, the disposable sample holder has a weight less than or equal to about 5 g.

Another aspect of the present disclosure provides a low-cost sample holder for use with PCR, comprising a substrate formed of a metallic material having a density between about 2.7 g/cm$^3$ and 3.0 g/cm$^3$. The substrate is configured to provide heat to one or more wells of the low-cost sample holder at a heating rate between about 5° C./s and 15° C./s. In an embodiment, the substrate comprises aluminum. In another embodiment, the low-cost sample holder further comprises a barrier layer formed of a first polymeric material over the substrate. In another embodiment, the one or more wells are formed of a second polymeric material joined to the first polymeric material.

Another aspect of the present disclosure provides a microplate for PCR, comprising a Peltier heating device and a substrate adjacent to the Peltier heating device, the substrate comprising a metallic material for heating PCR samples. The microplate further comprises a barrier layer adjacent to the substrate, the barrier layer formed of a first polymeric material. One or more wells are disposed adjacent to the substrate, the one or more wells for containing PCR samples. The one or more wells are formed of a second polymeric material sealed to the barrier layer. In an embodiment, the first polymeric material is different from the second polymeric material. In another embodiment, the first polymeric material is the same as the second polymeric material. In another embodiment, the substrate provides a PCR ramp rate of at least 5° C./second. In another embodiment, the substrate provides a PCR ramp rate of at least 10° C./second.

Another aspect of the present disclosure provides a microplate for PCR, comprising a substrate comprising a metallic material for heating PCR samples and a barrier layer adjacent to the substrate, the barrier layer formed of a first polymeric material. The microplate further comprises one or more wells adjacent to the substrate, the one or more wells for containing PCR samples. The one or more wells are formed of a second polymeric material sealed to the barrier layer. The microplate is configured to come in electrical contact with one or more electrical contact (e.g., bus bars) at one or more corrugated surfaces of the substrate. In an embodiment, the first polymeric material is different from the second polymeric material. In another embodiment, the first polymeric material is the same as the second polymeric material. In another embodiment, the one or more corrugated surfaces are disposed at finger-like projections (also "fingers" herein) of the substrate. In another embodiment, the one or more corrugated surfaces are formed from the fingers. In another embodiment, the substrate provides a PCR ramp rate of at least 5° C./second. In another embodiment, the substrate provides a PCR ramp rate of at least 10° C./second.

Another aspect of the present disclosure provides a microplate for PCR, comprising a heating device and a substrate adjacent to the heating device, the substrate comprising a metallic material for heating PCR samples upon the flow of current through the substrate. The microplate further comprises a barrier layer adjacent to the substrate, the barrier layer formed of a first polymeric material. One or more wells are disposed adjacent to the substrate, the one or more wells for containing PCR samples. The one or more wells are formed of a second polymeric material sealed (e.g., heat sealed, clamped) to the barrier layer. In an embodiment, the heating device is a Peltier heating device or a heating clamp. In another embodiment, the first polymeric material is different from the second polymeric material. In another embodiment, the first polymeric material is the same as the second polymeric material.

Another aspect of the present disclosure provides a method for conducting PCR, wherein data from the PCR and instructions for processing the data are located on a removable device. In an embodiment, both control and analysis instructions are provided in the removable device to allow a user to develop an experiment and analyze the results independently from a thermal cycler used for conducting PCR. In another embodiment, the removable device is a universal serial bus device. In another embodiment, the removable device is a removable memory disk. In another embodiment, the removable device is a compact flash, a serial advanced technology attachment interface, or a personal computer memory card international association interface. In another embodiment, the instructions on the removable device enable an identification of the type of hardware interfacing with the removable device and provide predetermined commands and/or instructions for performing PCR on the hardware.

Another aspect of the present disclosure provides a system for performing PCR, comprising a plurality of bus bars for electrically mating with a microplate or sample holder, and a microplate or sample holder as described above or elsewhere herein, alone or in combination. The microplate or sample holder is in electrical communication with, and removable from, the plurality of bus bars. The system further comprises a current application device for applying current to the microplate or sample holder. In an embodiment, the microplate or sample holder is in ohmic contact with the plurality of bus bars. In another embodiment, the microplate or sample holder comprises finger-like projections in electrical communication (or electrical contact) with the bus bars. In another embodiment, the finger-like projections have surfaces comprising crinkles. In another embodiment, the system further comprises a temperature sensor such as an infrared sensor, for measuring the temperature of the microplate or sample holder. In another embodiment, the system further comprises a plurality of temperature sensors for measuring the temperature of the microplate or sample holder in a plurality of thermal zones. In another embodiment, the system comprises at least nine sensors for measuring the temperature of the microplate or sample holder in nine thermal zones. In another embodiment, the plurality of temperature sensors provide continuous temperature measurements. In another embodiment, temperature variation across the microplate or sample holder is less than about 0.5° C.

Another aspect of the present disclosure provides a method for conducting PCR, comprising providing a microplate or sample holder as described above or elsewhere herein, alone or in combination, and conducting PCR on the sample. During PCR, the sample is heated at a ramp rate of at least about 5° C./second. In an embodiment, the method further comprises providing a sample to the microplate or sample holder before conducting PCR. In an embodiment, during PCR the sample is heated at a ramp rate of at least about 0.1° C./second. In another embodiment, during PCR the sample is heated at a ramp rate of at least about 0.5° C./second. In another embodiment, during PCR the sample is heated at a ramp rate of at least about 1° C./second. In another embodiment, during PCR the sample is heated at a ramp rate of at least about 5° C./second. In another embodiment, during PCR the sample is heated at a ramp rate of at least about 10° C./second. In another embodiment, during PCR the sample is heated at a ramp rate of at least about 15° C./second.

Another aspect of the present disclosure provides a method for performing PCR, comprising providing a microplate or sample holder as described above or elsewhere herein, alone or in combination, and conducting PCR on the sample. During PCR, the microplate or sample holder has well-to-well thermal uniformity of at least about +/−2° C., +/−1° C., +/−0.5° C., +/−0.2° C., +/−0.1° C., +/−0.05° C. without an external heating element or a Peltier heating block. In an embodiment, the method further comprises providing a sample to the microplate or sample holder before conducting PCR.

Another aspect of the present disclosure provides a method for conducting PCR, comprising providing a microplate or sample holder as described above or elsewhere herein, alone or in combination, and conducting PCR on the sample at a rate of at least about 0.1 PCR cycles per minute. In an embodiment, the method further comprises providing a sample to the microplate or sample holder before conducting PCR. In another embodiment, PCR is conducted on the sample at a rate of at least about 1 PCR cycle per minute. In another embodiment, PCR is conducted on the sample at a rate of at least about 2 PCR cycles per minute. In another embodiment, PCR is conducted on the sample at a rate of at least about 3 PCR cycles per minute. In another embodiment, PCR is conducted on the sample at a rate of at least about 6 PCR cycles per minute. In another embodiment, the method further comprises performing fluorescence measurement in an individual PCR cycle. In another embodiment, during PCR, the microplate or sample holder has well-to-well thermal uniformity of at least about +/−2° C., +/−1° C., +/−0.5° C., +/−0.2° C., +/−0.1° C., +/−0.05° C. without an external heating element or a Peltier heating block. In another embodiment, during PCR the sample is heated at a ramp rate of at least about 0.1° C./second. In another embodiment, during PCR the sample is heated at a ramp rate of at least about 0.5° C./second. In another embodiment, during PCR the sample is heated at a ramp rate of at least about 1° C./second. In another embodiment, during PCR the sample is heated at a ramp rate of at least about 5° C./second. In another embodiment, during PCR the sample is heated at a ramp rate of at least about 10° C./second. In another embodiment, during PCR the sample is heated at a ramp rate of at least about 15° C./second.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
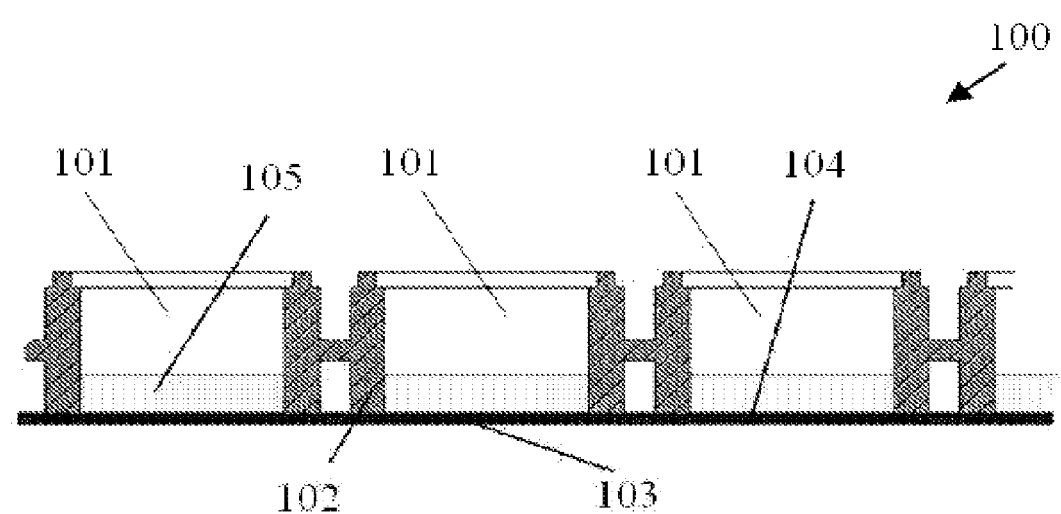
FIG. 1 is a schematic side-view of a microplate for polymerase chain reaction (PCR), in accordance with an embodiment of the invention.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

In some embodiments, microplate assemblies (also "microplates" herein) are provided for polymerase chain reaction (PCR). Microplates of the present disclosure may provide various advantages over current PCR systems, as rapid and accurate thermal control during PCR. In some embodiments, microplates are provided that can perform at least about 0.1, 1, 2, 3, 4, 5, 6, 7, 8, 9, 10, 20, 30, 40, 50, 60, 70, 80, 90, 100, 200, 300, 400, 500, 1000 PCR cycles per minute, in some cases with fluorescence measurements every cycle. In another embodiment, microplates are provided having an average heating ramp rate of at least about 0.01° C./second, or 0.1° C./second, or 1° C./second, or 2°

C./second, or 3° C./second, or 4° C./second, or 5° C./second, or 6° C./second, or 7° C./second, or 8° C./second, or 9° C./second, or 10° C./second, or 11° C./second, or 12° C./second, or 13° C./second, or 14° C./second, or 15° C./second, or 16° C./second, or 17° C./second, or 18° C./second, or 19° C./second, or 20° C./second, or 25° C./second, or 30° C./second, or 35° C./second, or 40° C./second, or 45° C./second, or 50° C./second, 100° C./second, or more. In another embodiment, microplates are provided having active control over thermal uniformity, producing thermal control to within +/−2° C., +/−1° C., +/−0.5° C., +/−0.2° C., +/−0.1° C., +/−0.05° C. or better.

In some embodiments, microplates may be consumable. In another embodiment, microplates may be recyclable. In another embodiment, microplates may be reusable. In another embodiment, microplates may be biodegradable. In another embodiment, the microplates may be non-consumable.

Microplates for Polymerase Chain Reaction (PCR)

An aspect of the present disclosure provides a microplate for polymerase chain reaction (PCR). In embodiments, the microplate comprises a substrate including a metallic material for heating PCR samples and a barrier layer disposed over the substrate, the barrier layer formed of a first polymeric material. The microplate further includes one or more wells for containing PCR samples, the one or more wells formed of a second polymeric material sealed to the barrier layer. In some cases, the first polymeric material is different from the second polymeric material. In an example, the first polymeric material has a different glass transition temperature than the second polymeric material. In other cases, the first polymeric material is the same as the second polymeric material. In an example, the first polymeric material has the same or substantially the same glass transition temperature as the second polymeric material.

In some embodiments, the substrate provides a PCR ramp rate (or heating rate) of at least about 0.01° C./second, or 0.1° C./second, or 1° C./second, or 2° C./second, or 3° C./second, or 4° C./second, or 5° C./second, or 6° C./second, or 7° C./second, or 8° C./second, or 9° C./second, or 10° C./second, or 11° C./second, or 12° C./second, or 13° C./second, or 14° C./second, or 15° C./second, or 16° C./second, or 17° C./second, or 18° C./second, or 19° C./second, or 20° C./second, or 25° C./second, or 30° C./second, or 35° C./second, or 40° C./second, or 45° C./second, or 50° C./second, or 100° C./second, or more.

In some embodiments, heating of PCR samples may be achieved by passing electric current through the substrate. In another embodiment, heating of PCR samples may be achieved by passing direct current (DC) through the substrate. In another embodiment, heating of PCR samples may be achieved by passing alternating current (AC) through the substrate.

In some embodiments, the substrate is separated from a PCR sample by 1 micrometer ("micron") or less, or 2 microns or less, or 3 microns or less, or 4 microns or less, or 5 microns or less, or 6 microns or less, or 7 microns or less, or 8 microns or less, or 9 microns or less, or 10 microns or less, or 11 microns or less, or 12 microns or less, or 13 microns or less, or 14 microns or less, or 15 microns or less, or 16 microns or less, or 17 microns or less, or 18 microns or less, or 19 microns or less, or 20 microns or less. In other embodiments, the substrate is separated from a PCR sample by at least about 0.1 microns, or 1 micron, or 2 microns, or 3 microns, or 4 microns, or 5 microns, or 10 microns, or 15 microns, or 20 microns, or 30 microns, or 40 microns, or 50 microns, or 100 microns, or 500 microns, or 1000 microns, or 5000 microns, or 10,000 microns, or more.

In some embodiments, the second polymeric material is heat-sealed to the barrier layer. In another embodiment, the first polymeric material is chemically compatible with the second polymeric material. In another embodiment, the metallic material comprises aluminum or an aluminum alloy.

In some embodiments, the substrate is for generating heat upon the flow of electrical current through the substrate. In another embodiment, the substrate is for generating heat upon the flow of direct current (DC) through the substrate. In another embodiment, the substrate is for generating heat upon the flow of alternating current (AC) through the substrate.

In some embodiments, the substrate is for increasing the temperature of a sample in the one or more wells at a rate between about 0.01° C./second and 100° C./second, or between about 0.1° C./second and 50° C./second, or between about 1° C./second and 35° C./second, or between about 3° C./second and 25° C./second, or between about 5° C./second and 15° C./second.

In some embodiments, the substrate includes a metallic material for heating PCR samples. The metallic material may have a resistivity between about $5 \times 10^{-9}$ ohm-m and $1 \times 10^{-6}$ ohm-m, or between about $1 \times 10^{-8}$ ohm-m and $1 \times 10^{-7}$ ohm-m, or between about $2 \times 10^{-8}$ ohm-m and $8 \times 10^{-8}$ ohm-m.

In some embodiments, the microplate can include one or more wells. In some cases, the microplate can include 1 well, or 2 wells, or 3 wells, or 4 wells, or 5 wells, or 6 wells, or 7 wells, or 8 wells, or 9 wells, or 10 wells, or 11 wells, or 12 wells, or 13 wells, or 14 wells, or 15 wells, or 16 wells, or 17 wells, or 18 wells, or 19 wells, or 20 wells, or 21 wells, or 22 wells, or 23 wells, or 24 wells, or 25 wells, or 26 wells, or 27 wells, or 28 wells, or 29 wells, or 30 wells, or 31 wells, or 32 wells, or 33 wells, or 34 wells, or 35 wells, or 36 wells, or 37 wells, or 38 wells, or 39 wells, or 40 wells, or 41 wells, or 42 wells, or 43 wells, or 44 wells, or 45 wells, or 46 wells, or 47 wells, or 48 wells, or 49 wells, or 50 wells, or 51 wells, or 52 wells, or 53 wells, or 54 wells, or 55 wells, or 56 wells, or 57 wells, or 58 wells, or 59 wells, or 60 wells, or 61 wells, or 62 wells, or 63 wells, or 64 wells, or 65 wells, or 66 wells, or 67 wells, or 68 wells, or 69 wells, or 70 wells, or 71 wells, or 72 wells, or 73 wells, or 74 wells, or 75 wells, or 76 wells, or 77 wells, or 78 wells, or 79 wells, or 80 wells, or 81 wells, or 82 wells, or 83 wells, or 84 wells, or 85 wells, or 86 wells, or 87 wells, or 88 wells, or 89 wells, or 90 wells, or 91 wells, or 92 wells, or 93 wells, or 94 wells, or 95 wells, or 96 wells, or 97 wells, or 98 wells, or 99 wells, or 100 wells, or 101 wells, or 102 wells, or 103 wells, or 104 wells, or 105 wells, or 106 wells, or 107 wells, or 108 wells, or 109 wells, or 110 wells, or 111 wells, or 112 wells, or 113 wells, or 114 wells, or 115 wells, or 116 wells, or 117 wells, or 118 wells, or 119 wells, or 120 wells, or 121 wells, or 122 wells, or 123 wells, or 124 wells, or 125 wells, or 126 wells, or 127 wells, or 128 wells, or 129 wells, or 130 wells, or more. In some embodiments, the microplate can include 1 or more, or 5 or more, or 10 or more, or 15 or more, or 20 or more, or 25 or more, or 30 or more, or 35 or more, or 40 or more, or 45 or more, or 50 or more, or 60 or more, or 70 or more or 80 or more, or 90 or more, or 100 or more, or 110 or more, or 120 or more, or 130 or more, or 140 or more, or 150 or more, or 200 or more, or 300 or more, or 400 or more, or 500 or more, or 1000 or more wells.

In an embodiment, the microplate may include 24 wells. In another embodiment, the microplate may include 48 wells. In another embodiment, the microplate can include 54 wells. In another embodiment, the microplate may include 72 wells. In another embodiment, the microplate may include 96 wells. The microplate can be disposable and/or recyclable.

In some embodiments, the microplate may include 24 wells, each well having a volume between 5 micro liter (µl) and 40 µl fill, or 96 wells, each well having a volume between about 0.5 µl and 5 µl.

In other embodiments, a microplate for polymerase chain reaction (PCR) comprises a substrate comprising a metallic material for heating PCR samples, a coating layer (also "barrier layer" herein) disposed over the substrate, the coating layer formed of a first polymeric material; and one or more wells formed of a second polymeric material sealed to the coating layer for containing PCR samples. In some embodiments, the metal substrate provides well-to-well thermal uniformity of +/−2° C. or better, or +/−1° C. or better, or +/−0.5° C. or better, or +/−0.2° C. or better, or +/−0.1° C. or better, or +/−0.05° C. or better, without the need for an external heating element or a Peltier heating block.

In other embodiments, a microplate for polymerase chain reaction (PCR) comprises a substrate comprising a metallic material for heating PCR samples; a coating layer disposed over the substrate, the coating layer formed of a first polymeric material; and one or more wells for containing PCR samples, the one or more wells formed of a second polymeric material sealed to the coating layer. In some embodiments, the metal substrate provides a heating efficiency sufficient to allow for at least 0.1 PCR cycles per minute, or at least 1 PCR cycle per minute, or at least 2 PCR cycles per minute, or at least 3 PCR cycles per minute, or at least 4 PCR cycles per minute, or at least 5 PCR cycles per minute, or at least 6 PCR cycles per minute, or at least 7 PCR cycles per minute, or at least 8 PCR cycles per minute, or at least 9 PCR cycles per minute, or at least 10 PCR cycles per minute, or at least 20 PCR cycles per minute, or at least 30 PCR cycles per minute, or at least 40 PCR cycles per minute, or at least 50 PCR cycles per minute, or at least 60 PCR cycles per minute, or at least 70 PCR cycles per minute, or at least 80 PCR cycles per minute, or at least 90 PCR cycles per minute, or at least 100 PCR cycles per minute, or at least 200 PCR cycles per minute, or at least 300 PCR cycles per minute, or at least 400 PCR cycles per minute, or at least 500 PCR cycles per minute, or at least 1000 PCR cycles per minute, in some cases including fluorescence measurement for every cycle.

In some embodiments, the microplate further includes a layer of an infrared radiation (IR)-normalizing material at a side of the substrate opposite the contact layer. The IR normalizing layer may aid in increasing IR emissivity, thereby providing for more efficient thermal regulation of the microplate and the one or more wells during PCR. In another embodiment, the microplate may comprise a layer of an IR-normalizing material at a side of the substrate opposite the coating layer. In some embodiments, the IR-normalizing layer may have a thickness less than about 10 micrometers ("microns"), or less than about 5 microns, or less than about 1 micron, or less than about 0.5 microns, or less than about 0.1 microns.

In some embodiments, the microplate may have a thickness less than about 0.1 mm, or less than about 0.2 mm, or less than about 0.3 mm, or less than about 0.4 mm, or less than about 0.5 mm, or less than about 0.6 mm, or less than about 0.7 mm, or less than about 0.8 mm, or less than about 0.9 mm, or less than about 1 mm. In another embodiment, the microplate may have a thickness between about 0.1 mm and 100 mm, or between about 0.2 mm and 20 mm, or between about 0.3 mm and 10 mm, or between about 0.4 mm and 0.6 mm.

In some embodiments, the coating layer may have a thickness less than about 10 micrometers ("microns"), or less than about 5 microns, or less than about 1 micron, or less than about 0.5 microns, or less than about 0.1 microns.

Another aspect of the present disclosure provides disposable sample holders for use with polymerase chain reaction (PCR). The disposable sample holders in some cases are formed of a recyclable material, such as a polymeric material, a metallic material (e.g., aluminum), or a composite material.

In some embodiments, a disposable sample holder comprises an aluminum substrate coated with a first polymeric material and a plurality of wells heat-sealed to the first polymeric material. The plurality of wells can be formed of a second polymeric material compatible with the first polymeric material.

In some cases, a disposable sample holder comprises an aluminum-containing substrate for providing heat to a plurality of wells of the disposable sample holder. The disposable sample holder can have a weight less than or equal to about 100 g, or 90 g, or 80 g, or 70 g, or 60 g, or 50 g, or 40 g, or 30 g, or 20 g, or 15 g, or 10 g, or 5 g, or 4 g, or 3 g, or 2 g, or 1 g, or lower. In some embodiments, the disposable sample holder is a single-use sample holder.

Another aspect of the present disclosure provides a low-cost sample holder for use with polymerase chain reaction (PCR). The low-cost sample holder can comprise a substrate formed of a metallic material having a density between about 2.0 g/cm$^3$ and 4.0 g/cm$^3$, or 2.7 g/cm$^3$ and 3.0 g/cm$^3$. The substrate can be configured to provide heat to one or more wells of the low-cost sample holder at a heating rate between about 0.01° C./second and 100° C./second, or between about 0.1° C./second and 50° C./second, or between about 1° C./second and 35° C./second, or between about 3° C./second and 25° C./second, or between about 5° C./second and 15° C./second. In some embodiments, the substrate includes aluminum. In some situations, the low-cost sample holder further includes a barrier layer formed of a first polymeric material over the substrate. The one or more wells of the low-cost sample holder may be formed of a second polymeric material joined to the first polymeric material.

FIG. 1 is a schematic cross-sectional side view of a microplate 100, in accordance with an embodiment of the invention. The microplate 100 includes a plurality of wells 101 (or well-like structures) in a moulding 102 comprising one or more tubes formed of a polymeric material, such as polypropylene. The tubes are attached to a surface of a metal plate 103. In some embodiments, the tubes are attached to the surface of the metal plate 103 with the aid of a coating layer (or barrier layer) 104 formed of a polymeric material that can be compatible with the material of the tubes of the moulding 102. The metal plate may be formed of an electrically resistive material. In some embodiments, the metal plate may be formed of aluminum or an aluminum alloy. The microplate of FIG. 1 has an assay 105 disposed in each of the wells.

In some cases, the moulding 102 can be formed from a single-piece polymeric material. The moulding 102, in some cases, is formed by injection moulding. In some situations, the moulding 102 can be formed of a plurality of pieces attached to one another (such as by welding or with the aid of an adhesive).

With continued reference to FIG. 1, the wells 101 are at least partly defined by sidewalls of the moulding 102 at least partially formed of a polymeric material. The moulding 102 may have a bottom surface of the moulding resting against the metal plate 103. This can provide for efficient thermal control in each of the wells.

In some embodiments, the moulding 102 can be secured to the metal plate 103 with the aid of a bonding material, such as an adhesive. In other embodiments, the moulding 102 is secured to the metal plate 103 with the aid of a clamp or fastener (not shown).

Microplate Heating

Another aspect of the present disclosure provides a microplate (or consumable) having wells for polymerase chain reaction (PCR) heating. In some embodiments, the consumable can be heated by passing an electrical current through the microplate. The microplate can be heated for a predetermined time period. Sample processing, including heating, can be regulated by a computer system having one or more processors for executing machine-readable instructions stored in a memory location of the computer system.

Heat can be generated by passing a current through the microplate of FIG. 1. Heating in some cases is resistive heating. The rate of heating or cooling can be adjusted by varying the current passing through at least a portion of the microplate, or varying the electrical potential applied across the microplate.

In some embodiments, a disposable microplate (also "consumable" herein) may include a coated metal plate with a polymer moulding attached to the metal plate. The metal plate may be coated with a polymeric material that is compatible with the moulding. The polymer moulding may be formed of a polymeric material. The consumable may, in itself, be a heating element. The consumable may be directly heated by passing electrical current through the metal plate. The consumable may include liquid samples or assays that are in close contact with the plate, separated from the plate by a layer of polymer, such that heat transfer to and from the samples is fast and controllable. In some embodiments, the layer of polymer may have a thickness of about 10 microns or other thickness provided herein (see above).

In some embodiments, the consumable may be heated by passing electrical current through the consumable along a number of different possible electric flow paths. In another embodiment, the contact fingers at the ends of the plate are connected to a system of bus bars. These bus bars are the single-turn secondary windings of four transformers. The consumable is configured to rest on (or come into electrical contact with) the bus bars. In some embodiments, the consumable is removable from the bus bars. In another embodiment, a fixed plate of similar geometry to the described consumable is permanently attached to the bus bars.

In some embodiments, the low current primary drive to each transformer is proportionally controlled using phase-angle triggering of triac devices. Also, by using twin primary windings, the relative phase of the drive to each transformer can be controlled.

In some embodiments, current passing through the plate are high and voltage applied to the plate are low. In some embodiments, current passing through the plate is up to about 50 A, or 100 A, or 150 A, or 200 A, or 300 A, or 400 A, or 500 A, or 600 A, or 700 A, or 800 A, or 900 A, or 1000 A per transformer. In another embodiment, voltage applied to the plate is between about 0.01 volts ("V") and 20 V, or between about 0.1 V and 10 V, or between about 0.1 V and 1 V, or between about 0.25 V and 0.5 V.

In some embodiments, heating is by resistive heating. In some cases, resistive heating is with the aid of direct current (DC). In other cases, resistive heating is with the aid of alternating current (AC).

A microplate can include N rows by M columns of wells, wherein 'N' and 'M' are integers greater than zero. In some cases, N is at least 1, or 2, or 3, or 4, or 5, or 6, or 7, or 8, or 9, or 10, or 20, or more, and M is at least 1, or 2, or 3, or 4, or 5, or 6, or 7, or 8, or 9, or 10, or 20, or more. The rows can be orthogonal to the columns, or may be angularly disposed in relation to the columns at an angle greater than 0° and less than 90° in relation to the columns. For instance, the rows can be angularly disposed at an angle of about 45° in relation to the columns.

Figure 10:
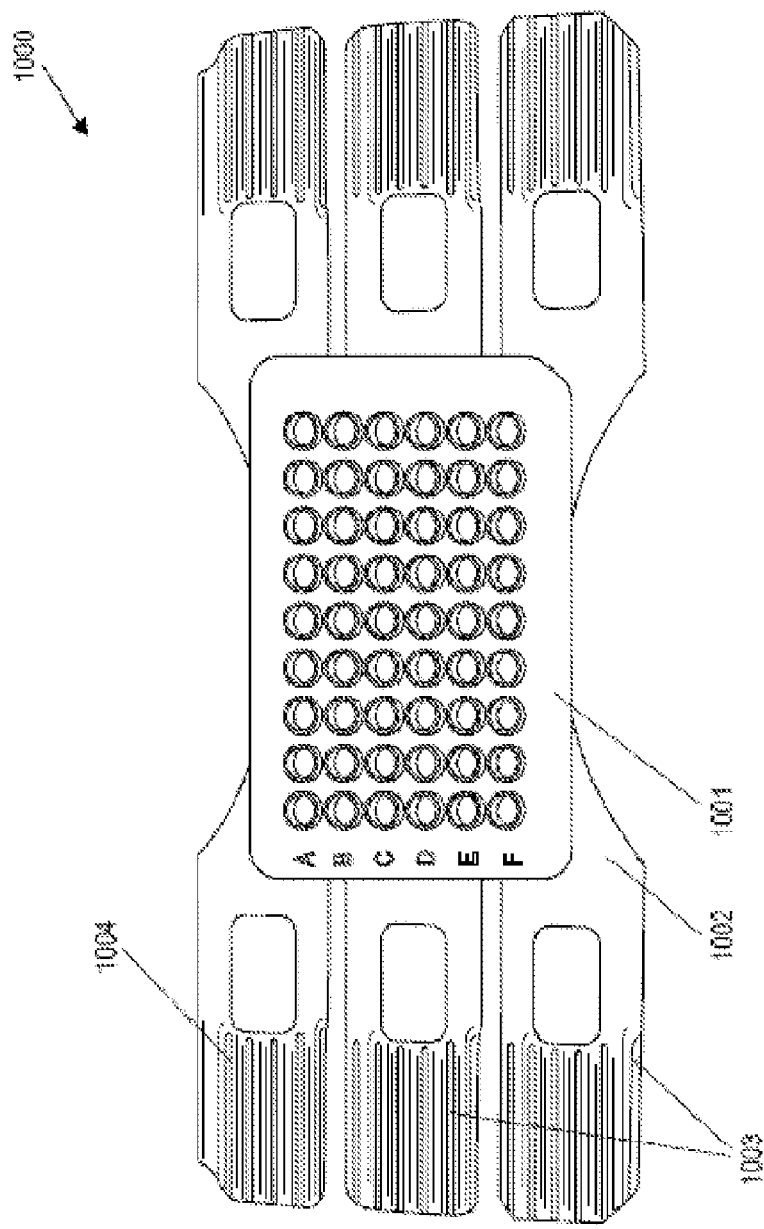
FIG. 10 shows a microplate having 54 wells, in accordance with an embodiment of the invention.

For example, a microplate can include 3 rows by 3 columns (3×3) of wells, or 9 total wells. As another example, a microplate can include 3×3, 4×6, 6×4, 9×6 or 6×9 wells. FIG. 10 shows a microplate 1000 having 6 rows by 9 columns of wells 1001, or 54 total wells. The wells are formed of a polymeric material and are disposed adjacent to a substrate 1002 formed of a metallic material (e.g., aluminum). The substrate 1002 comprises a plurality of fingers (or finger-like projections) 1003. Each finger 1003 has a top surface (facing the wells 1001) and a bottom surface. A top surface of each of the fingers (or micro-plates) 1003 has a wave pattern that defines a crinkle 1004 on the top surface. A bottom surface (not shown) of each of the fingers 1003 can have a wave pattern defining a crinkle. At least a portion of the top and bottom surfaces of the fingers are configured to come in contact with bus bars for facilitating the flow of electrical current through the microplate 1000 during PCR. In some cases, the crinkles 1004 can be precluded. In other cases, the surfaces of the fingers 1003 are roughened.

In some embodiments, a crinkle has a corrugation between about 0.1 micrometers ("microns") and 1 centimeter, or 1 micron and 10 millimeters ("mm"). In other embodiments, a crinkle has a corrugation of at least about 0.1 microns, or 1 micron, or 10 microns, or 100 microns, or 1 mm, or 10 mm, or 100 mm.

In some embodiments, a microplate includes a plurality of wells adjacent to a substrate. The substrate is formed of a metallic material, such as aluminum, and the wells are at least partly defined by a polymer matrix. In some cases, the polymer matrix defines each individual well. In other cases, the polymer matrix defines the one or more sidewalls of a well, but a bottom portion of a well is defined by the substrate. In some cases, the bottom portion of a well comprises a layer of a polymeric material adjacent to the substrate.

The microplate includes finger-like projections (see FIG. 10) for enabling the microplate to come in electrical communication with bus bars of a system for facilitating the flow of electrical current through the microplate. In some cases, a resistance between the microplate and the plurality of bus bars is minimized, and in some cases rendered ohmic, with the aid of wrinkles (or ridges) on surfaces of the finger-like projections configured to come in contact with the bus bars. The finger-like projections of the microplate can be tightly clamped to the bus bars.

In some cases, a microplate comprises fingers formed to have a wave pattern on their surfaces, thereby forming a crinkle. The crinkle can aid in removing any oxide layer formed on one or more surfaces of the fingers, which aids in improving the electrical contact between the fingers and the bus bars.

In some cases, a system for facilitating PCR can include a microplate, as described herein, and a temperature sensor for measuring the temperature in one or more zones of the microplate. The temperature sensor can be one or more thermocouples in electrical contact with the one or more zones. A thermocouple can be in electrical contact with a thermal zone. Alternatively, the temperature sensor can be an infrared sensor for measuring the temperature of one or more zones of the microplate. The infrared ("IR") sensor can be a non-contact IR sensor and configured to measure the temperature of a metallic substrate of the microplate.

The system can include at least 1, or 2, or 3, or 4, or 5, or 6, or 7, or 8, or 9, or 10, or 15, or 20, or 30, or 40, or 50, or 100, or more sensors for measuring the temperature of a microplate. The number of sensors used for temperature measurements can be equal to the number of thermal zones in the microplate. For example, the system can include nine sensors for measuring the temperature in each of nine thermal zones of a microplate.

A temperature sensor can provide continuous measurement of the temperature in a thermal zone of a microplate. In some cases this can provide for calibration to deliver a more accurate reading. Alternatively, a temperature sensor can provide intermittent temperature measurements, such as a temperature measurement at least every 0.01 seconds, 0.1 seconds, 1 second, 10 seconds, 30 seconds, 1 minute, 10 minutes, 30 minutes, 1 hour, 2 hours, 3 hours, 4 hours, 5 hours, 6 hours, 12 hours, 1 day, 2 days, or more. The sensors can provide feedback to determine how much heat is required for a particular zone of the plate.

In some embodiments, the temperature variation across a microplate is less than about 10° C., or 5° C., or 1° C., or 0.9° C., or 0.8° C., or 0.7° C., or 0.6° C., or 0.5° C., or 0.4° C., or 0.3° C., or 0.2° C., or 0.1° C., or lower. This enables the definition of temperature (or thermal) zones for accurate thermal control in each zone.

Microplates provided herein are configured for heating to enable PCR. Some embodiments provided microplates in electrical communication with a source of electrons to enable heating, which may be provided with the aid of an electrical current ("current") application member. Together, a microplate, a current application device and any other apparatuses (e.g., bus bars) for bringing the microplate in electrical contact with the current application device define an electrical flow path, or an electrical circuit ("circuit"). The current application device can be configured for either DC or AC modes of operation.

With reference to FIGS. 2-5, a consumable (center) with 24 wells is provided, in accordance with an embodiment of the invention. Power supply units (PSU) are also illustrated. The PSUs may be AC or DC power supply units. FIGS. 2-5 illustrate various transformer drive patterns for providing heat to the consumable. In some embodiments, a system is provided using a 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or more transformer drive patterns. In some embodiments, a system is provided using 12 transformer driver patterns. The arrows associated with the PSUs in FIGS. 2-5 indicate the relative phasing of the active PSUs in the corresponding mode. The PSU or PSUs without an associated arrow are off in that mode. A particular heating pattern is a function of the phasing of each of the PSUs.

Figure 2:
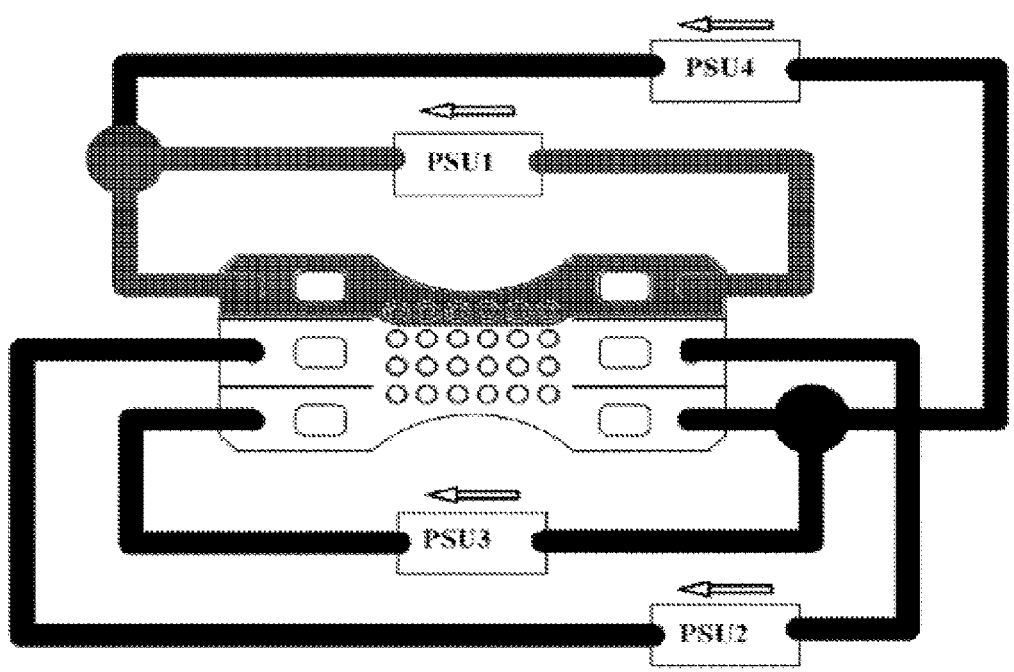
FIG. 2 schematically illustrates a transformer drive pattern for providing heat to a consumable, in accordance with an embodiment of the invention.
Figure 3:
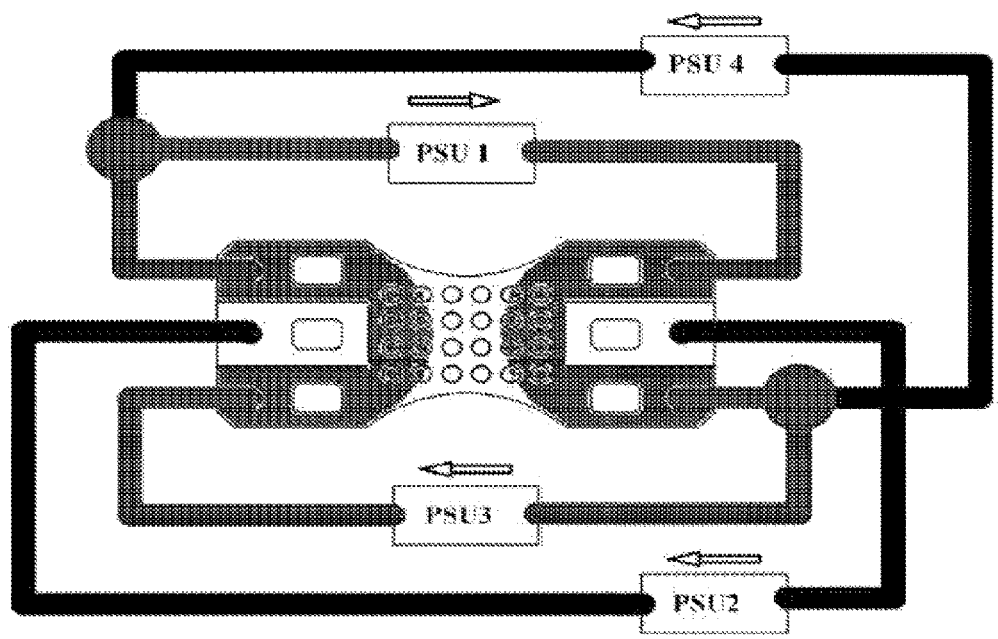
FIG. 3 schematically illustrates a transformer drive pattern for providing heat to a consumable, in accordance with an embodiment of the invention.
Figure 4:
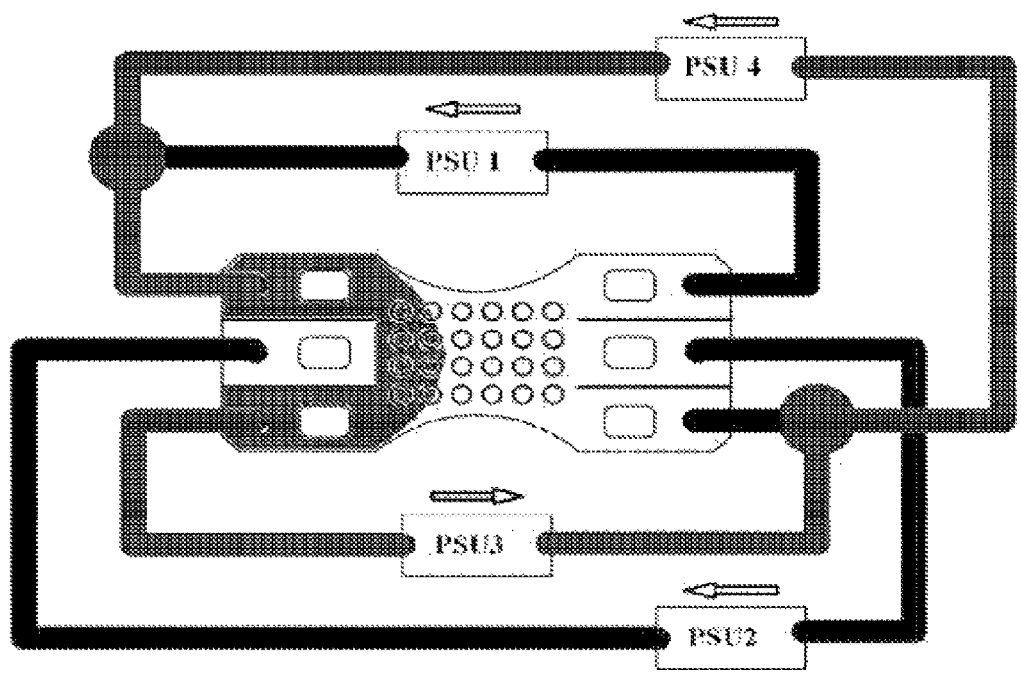
FIG. 4 schematically illustrates a transformer drive pattern for providing heat to a consumable, in accordance with an embodiment of the invention.
Figure 5:
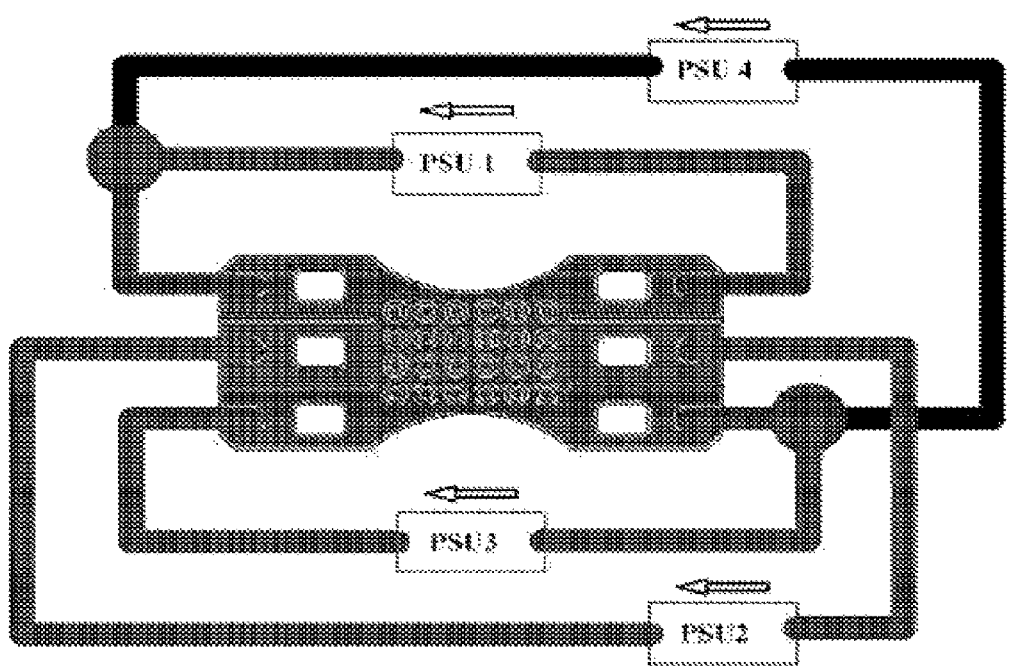
FIG. 5 schematically illustrates a transformer drive pattern for providing heat to a consumable, in accordance with embodiments of the invention.

With reference to FIG. 2, in a first configuration of relative phasing of PSU1, PSU2, PSU3 and PSU4, heat is provided to a top portion of the consumable. With reference to FIG. 3, in a second configuration of relative phasing of PSU1, PSU2, PSU3 and PSU4, heat is provided to side portions of the consumable. With reference to FIG. 4, in a third configuration of relative phasing of PSU1, PSU2, PSU3 and PSU4, heat is provided to a left side (when looking from the top) of the consumable. With reference to FIG. 5, in a fourth configuration of relative phasing of PSU1, PSU2, PSU3 and PSU4, heat is provided to all or substantially all of the consumable.

In embodiments, the heating pattern of a consumable may be the product of a balance between heating rates and cooling rates of the consumable. That is, if the center of the consumable is cooled more rapidly that it is heated, a cooling effect will ensue. If the sides of the consumable are heated more rapidly than the center, the center will remain cooler relative to the sides of the consumable. In embodiments, heating rates and cooling may be dependent on various factors, such as, e.g., the modes of heat transfer (i.e., conductive, convective, or radiative) and the interplay between the modes; heat transfer coefficients; thermal mass; initial temperature; and PSU power.

With reference to FIGS. 2-5, the flow of current may produce a predetermined heating pattern. The use of different current paths through the metal plate may enable use of the consumable as plate heating zones for zonal control, enabling active control of thermal uniformity.

In some embodiments, the plate is cooled from below by means of high pressure air jets, such as 1 or more, or 2 or more, or 3 or more, or 4 or more, or 5 or more, or 10 or more high pressure air jets. The jets may be switched on and off individually, and air pressure may be controlled to give proportionality in cooling. This may effectively give zonal control over the applied cooling power. The heating system may also be used, even when cooling, to actively maintain overall thermal uniformity. In some embodiments, compressed air may be supplied from a building air supply, or a small local compressor, or by using 4 miniature air pumps with pulse-width modulation (PWM) control. In all cases the pressure employed is controlled between 0 psi and 50 psi and the air is directed onto the bottom of the plate by nozzles, such as 4 small, 0.7 mm diameter nozzles, which produce high velocity jets to penetrate the boundary layer of the flat plate.

Clamp and Clamping Method

In some embodiments, in order to operate at low voltage and low plate resistance, contact between the removable plate (e.g., microplate) and the fixed bus bars is critical.

In some embodiments, the plate when located in the machine not only provides the container for the test samples, it is also a resistive heating element. In some instances, the ends of the plate are crinkled. Heating can be induced upon the flow of an electrical current through the metallic (e.g., aluminum) base of the plate. In some cases, the connections between the plate and the rest of the circuit need to be of low resistance when compared to the resistance of the plate so that the induced heating will not occur in the rest of the circuit.

To achieve a low electrical resistance, the metallic fingers or finger-like projections (e.g., aluminum fingers) of the plate can be tightly clamped to high conductivity bus bars of a current application device. Such clamping can provide ohmic, near ohmic or substantially ohmic contact between the fingers and the bus bars, which can provide for improved heating. In addition to the force required to tightly clamp the fingers, the fingers can be formed to have a wave pattern on their surface (e.g., one or more crinkles), such that as they are clamped flat there can be a wiping action on the surface of the plate which breaks down any oxide (e.g., metal oxide)

or contamination that may have coated the surface. This advantageously provides preferable electrical connection to the fingers.

There are a number of elements to this arrangement, such as the provision of high force. The force provided by the clamp, in some cases, can be greater than 1 Newton (N), 2 N, 3 N, 4 N, 5 N, 6 N, 7 N, 8 N, 9, N, 10 N, 20 N, 30 N, 40 N, 50 N, 60 N, 70 N, 80 N, 90 N, 100 N, 200 N, 300 N, 400 N, 500 N, 600 N, 700 N, 800 N, 900 N, 1000 N, 2000 N, 3000 N, 4000 N, 5000 N, or 10,000 N on a repeatedly made connection. In some instances, this is achieved by using an over center toggle-type clamp. In some embodiments, the clamp has a built-in spring system which reduces the precision needed to set up the clamp.

Figure 18:
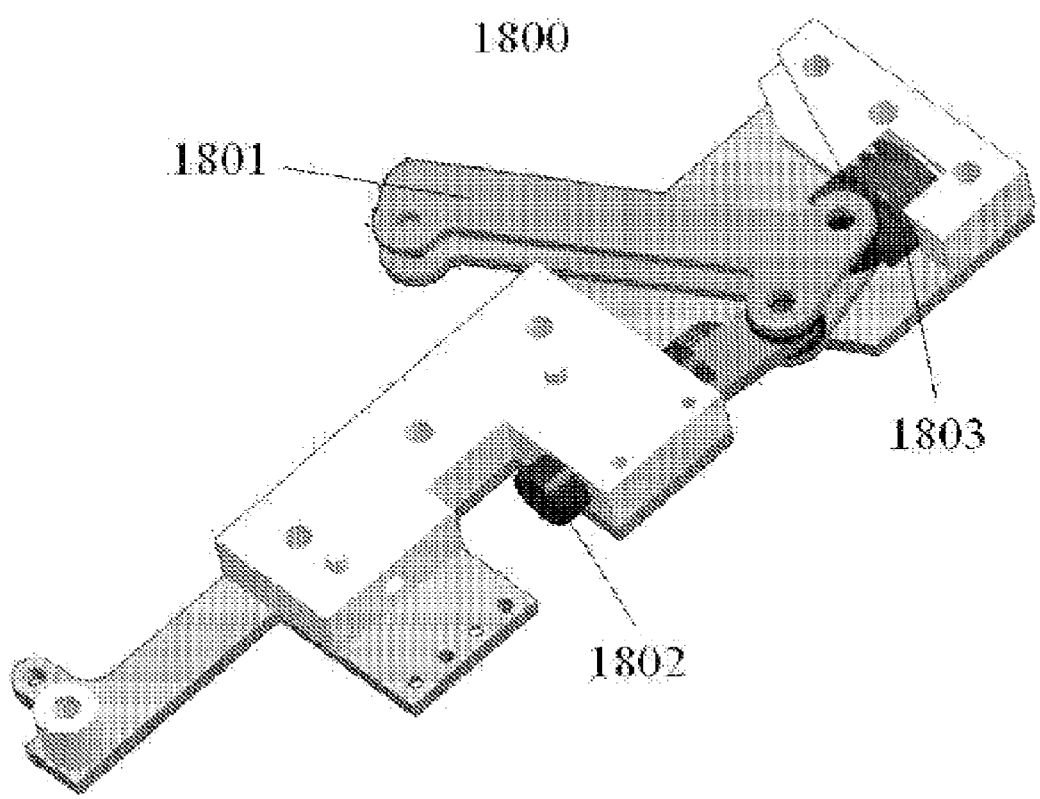
FIG. 18 schematically illustrates an exemplary clamp, in accordance with an embodiment of the invention.

FIG. 18 shows a clamp 1800 suitable for forming a low resistance electrical connection between a microplate and a bus-bar in a thermocycler. The clamp 1800 can operate with any microplate disclosed herein. The clamp 1800 comprises a handle 1801 that is coupled to a spring-loaded pivot, and a ram 1802. In some instances, the clamp comprises a spring 1803. The spring can be a Belleville spring washer (also called a coned-disc spring or cupped spring washer).

Operation of the clamp can force the microplate into contact with the bus-bar. In an example, during use, a user moves the handle 1801 along a linear direction, which causes the ram 1802 to come in contact with a bus bar. Such action can clamp the bus bar against microplate. Upon completion of heating, the handle can be moved in a reverse direction to decouple (or dislodge) the microplate from the bus bars.

The handle 1801 can be operated manually or with the aid of an actuation mechanism, such as, for example, a motor. In some examples, the handle 1801 is coupled to a motor, and a system for automating PCR moves the handle along a linear direction to clamp the microplate against the bus bar and to release the microplate from the bus bar once PCR is complete.

The clamp 1800 can be part of a thermocycler. The thermocycler can include a current application device that is configured to provide an electrical current to a microplate through bus bars in electrical contact with the microplate. The clamp can be actuated with the aid of a motor of the thermocycler that is coupled to the handle 1801. The thermocycler can include a computer processor that can execute machine-executable code to use the clamp 1800 to provide electrical contact between the microplate and the bus bars.

The present disclosure provides a method for forming a low resistance electrical connection between a microplate and a bus-bar in a thermocycler. The method comprises clamping the microplate to the bus-bar with the clamp comprising the handle 1801 and a ram 1802.

In some embodiments, the clamp 1800 is an over center toggle type clamp. In some embodiments, the clamp provides control over the force applied by the ram over a range of adjustments. In some embodiments, the clamp is adjusted such that the clamp can be closed by hand and the clamp is capable of forming a low resistance electrical connection between the microplate and the bus-bar.

In some instances, the clamp becomes worn over time (e.g., from repeated use). In one aspect, use of a spring-loaded pivot in the clamp allows the clamp to exert a suitable force when the clamp becomes warn. In one aspect, use of a spring-loaded pivot in the clamp decreases or eliminates the need to adjust the clamp when the clamp becomes worn.

In some embodiments, the clamp is capable of exerting any suitable force (e.g., suitable for deforming the crinkles and/or forming a suitable low resistivity electrical connection). In some embodiments, the clamp is capable of exerting a force of about 100, about 200, about 400, about 600, about 800, about 1,000, about 1,250, about 1,500, about 1,750, about 2,000, about 2,500, about 3,000, about 4,000 Newtons and the like. In some embodiments, the clamp is capable of exerting a force of at least 100, at least 200, at least 400, at least 600, at least 800, at least 1,000, at least 1,250, at least 1,500, at least 1,750, at least 2,000, at least 2,500, at least 3,000, at least 4,000 Newtons and the like. In some embodiments, the clamp is capable of exerting a force of at most 100, at most 200, at most 400, at most 600, at most 800, at most 1,000, at most 1,250, at most 1,500, at most 1,750, at most 2,000, at most 2,500, at most 3,000, at most 4,000 Newtons and the like. In some embodiments, the clamp is capable of exerting a force between 100 and 4,000 Newtons, between 1,000 and 3,000 Newtons, between 1,500 and 2,000 Newtons, and the like.

In an embodiment, the plate is clamped to gold-plated contacts on the bus bars using 6 miniature hydraulic rams driven by a master cylinder actuated by an electric ball screw. The rams may each exert a force of at least about 1 Newton (N), 2 N, 3 N, 4 N, 5 N, 6 N, 7 N, 8 N, 9, N, 10 N, 20 N, 30 N, 40 N, 50 N, 60 N, 70 N, 80 N, 90 N, 100 N, 200 N, 300 N, 400 N, 500 N, 600 N, 700 N, 800 N, 900 N, 1000 N, 2000 N, 3000 N, 4000 N, 5000 N, or 10,000 N, which can produce sufficient deformation of the aluminum to disrupt the oxide film that may be found on the surface of the metal, and provide substantially low resistance contacts between the plate and the bus bars. Other clamping methods may be used, such as, for example, hydraulic or screw clamping.

In some instances, slight doming of the clamping ram provides an annular ring of contact, rather than a point or face contact which delivers both high contact force and preferable contact area to help provide repeatable low resistance connections. Putting undulations (or preform) in the surface of the plate in the area of the clamp can enable the material to move and wipe across clamping surfaces as it is crushed flat by the clamp ram. This process of wiping can be used on various connectors to produce low resistance contacts. In some cases, the preform may be crushed. The size and depth of the preform may be important in determining the wiping action. With the aid of crinkles, the resistant between the microplate and the bus bars can be minimized, and in some cases minimized to below the resistance of an electrical circuit having the microplate and a current application device.

In some embodiments, the clamp is capable of deforming the microplate, thereby disrupting an oxide film on the surface of the microplate. In some embodiments, the electrical resistance at the interface of the microplate and the bus-bar is less than the resistance of the microplate. In some embodiments, the microplate is consumable.

An aspect of the present disclosure provides a system for performing polymerase chain reaction (PCR), comprising: (a) a plurality of bus bars for electrically mating with a microplate; (b) a microplate, the microplate comprising a metallic material for heating a sample during PCR; (c) a clamp, the clamp comprising a spring-loaded pivot and a ram, wherein the clamp is capable of forcing the microplate in electrical communication with and removable from the bus bars; and (d) a current application device for applying current to the microplate.

In some embodiments, the microplate is in ohmic contact with the plurality of bus bars. In some embodiments, the microplate comprises finger-like projections in electrical communication with the bus bars. In some embodiments, the finger-like projections have surfaces comprising crinkles. In some embodiments, the system further comprises an infrared sensor for measuring the temperature of the microplate. In some embodiments, the system further comprises a plurality of temperature sensors for measuring the temperature of the microplate in a plurality of thermal zones. In some embodiments, the plurality of temperature sensors provide continuous temperature measurements. In some embodiments, temperature variation across the microplate is less than 0.5° C.

Temperature Measurement and Control

In some embodiments, the temperature of the plate may be measured from below the plate using a 3×3 array of thermopile-type non-contact sensors. In another embodiment, temperature measurements can be made with the aid of at least 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30, or 31, or 32, or 33, or 34, or 35, or 36 or more thermopile-type non-contact sensors. In another embodiment, temperature measurements can be made with a number of sensors selected to match the number of wells.

Figure 6:
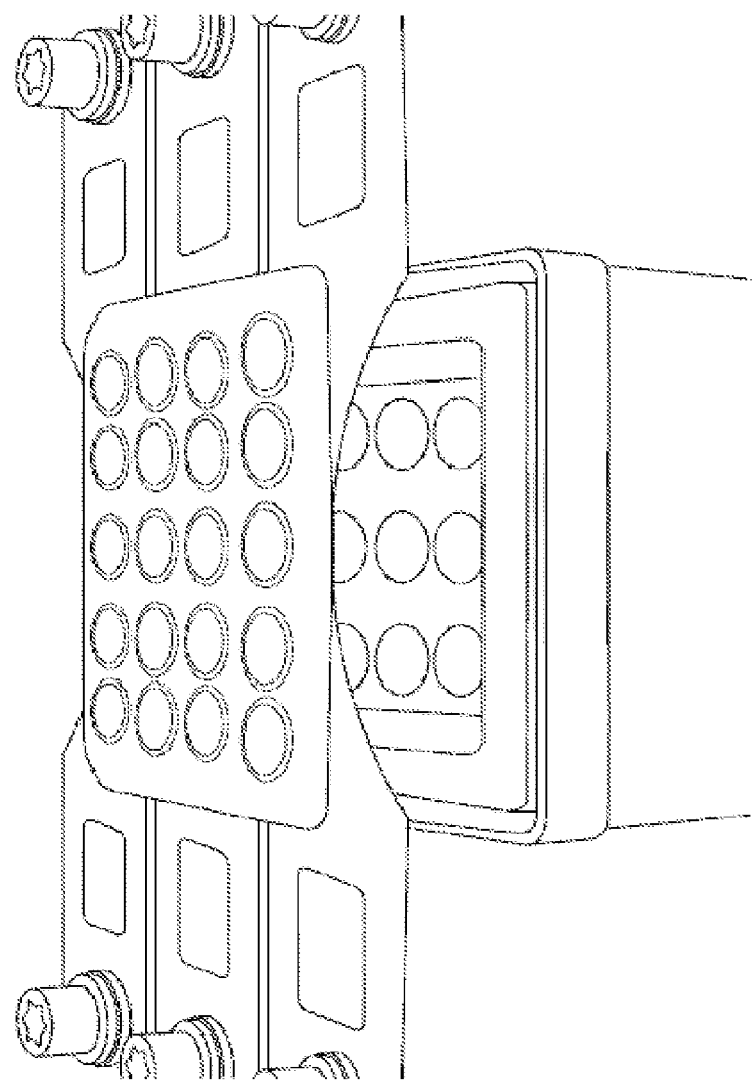
FIG. 6 shows a sensor block, in accordance with an embodiment of the invention.

FIG. 6 shows sensors on a mounting block, in accordance with an embodiment of the invention. In some situations, the bottom of the plate has an epoxy primer coating to normalize an infrared emissivity of the plate, which may aid in accurate sensor measurement. In other situations, the bottom of the plate does not include an epoxy primer. Temperature measurements can be made with the aid of a system operatively coupled to thermocouples in thermal contact with one or more wells.

In some embodiments, there is no one-to-one mapping between the sensors and the heating zones. In another embodiment, a computer uses information from the sensors to select the optimum transformer drive pattern from a predetermined number of programmed options, such as 12 programmed options. In another embodiment, the transformer drive pattern is updated about 50 times per second. In another embodiment, the transformer drive pattern is updated at least about 5, or 10, or 20, or 30, or 40, or 50, or 60, or 70, or 80, or 90, or 100 times or more per second.

Infra-red thermopile measurement of temperature; one embodiment uses an array of non-contact infra-red sensors to measure the temperature of the plate's aluminum base plate. There are 9 sensors in our current array which are used to measure the temperature in nine zones of the plate. These temperatures are used to control the heating system and produce the heating pattern desired. The infra-red sensors are industry standard parts but they only can measure as standard to an accuracy of about 1 degree. It is desirable to obtain times that accuracy of measurement; thus one embodiment individually calibrates each sensor across a range then uses this information to calculate a more accurate reading. This "calibration" of a sensor requires a number of points to be measured and these are used to populate an algorithm which extrapolates between them to give a value that is more accurate. This embodiment is advantageous based at least in part on the use of the "calibration" and the algorithm in combination to deliver a more accurate reading.

Heating control algorithm; the heating system consists of a multi-zone resistive heating element which can be heated in a number of different ways to provide heat into multiple zones. The temperature of the zones is measured by an array of non-contact infra-red sensors which provide continuous measurement. Control of the system is complex because you can't heat just one zone without heating others both directly by flowing current through the zone and indirectly through heat transfer from neighboring zones. An algorithm has been developed that provides this complex control using feedback from the thermal sensors to determine how much heat is required and where. This algorithm not only gets the plate to the desired temperature quickly it is used to keep the temperature variation across the plate to a minimum so that all the test samples effectively see the same experimental conditions, important when you are trying to compare results across test plates and from plate to plate. The novelty here is in the actual nature of the algorithm as well as its use.

In some embodiments, a system is provided for controlling heating and cooling of a plate and consumable in thermal communication with the plate. In another embodiment, a system having software is provided for controlling heating and cooling of a plate and consumable in thermal communication with the plate. In another embodiment, a system is provided for maintaining thermal uniformity across an active region of the plate, whilst following a programmed temperature profile.

In some embodiments, when a user has filled the tubes on the plate with reagents, the tops of the tubes are sealed using a cover, such as a transparent sealing film. This may allow the measurement of fluorescence to be made from above the plate to follow the progress of PCR. A charge-coupled device (CCD) camera may be used to record fluorescent output. The CCD camera may have a filter wheel. Radiation for excitation may be provided by one or more excitation sources, such as light emitting diodes (LED's) with filters.

As an alternative, a microplate may be heated or cooled with the aid of a heating device employing Peltier heating. In some cases, the microplate of FIG. 1 may be used with the aid of a Peltier heating element in the vicinity of an underside of the microplate. In such a case, the metal plate may permit heat transfer to each of the wells (or chambers) of the microplate. In some cases, a microplate may be in thermal communication with a Peltier heating element, which may transfer heat from one side of the heating element to the other side of the heating element against a temperature gradient upon the consumption of electrical energy.

Figure 7:
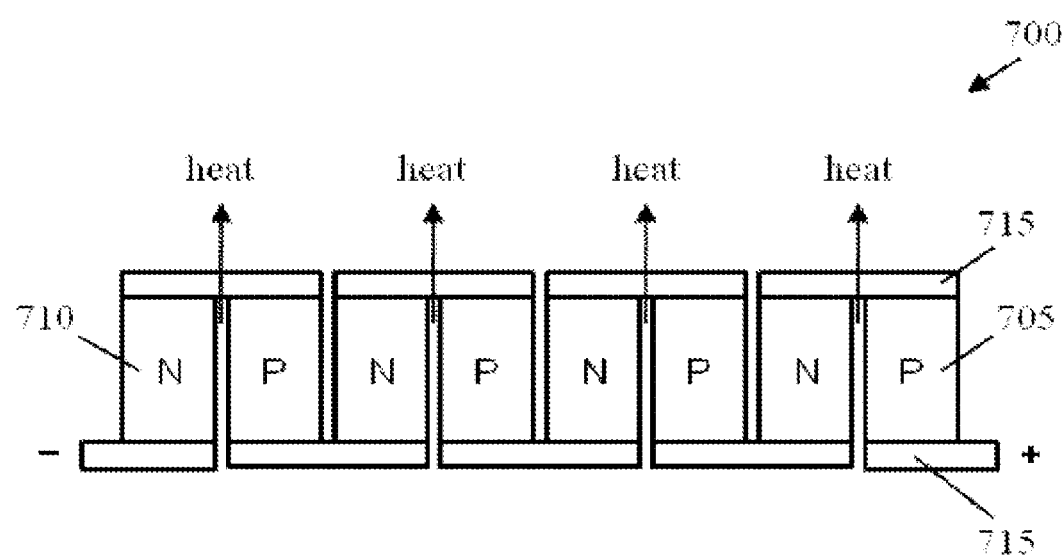
FIG. 7 shows a Peltier heating device, in accordance with an embodiment of the invention.

FIG. 7 shows a Peltier heating element 700 having a plurality of semiconductor-containing elements (or "pellets") that are chemically doped n-type ("N") 705 or p-type ("P") 710.

Figure 8:
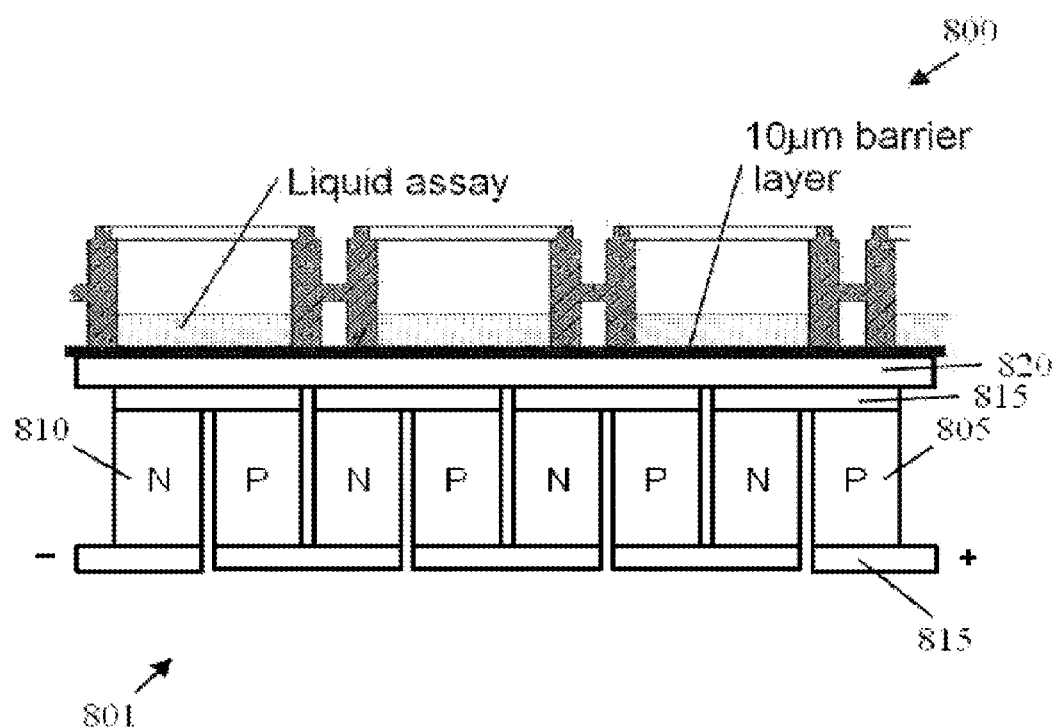
FIG. 8 shows a microplate and a Peltier heating device adjacent to the microplate, in accordance with an embodiment of the invention.

FIG. 8 shows a microplate 800 having a Peltier heating device 801 below the microplate 800. The Peltier heating device 801 may include p-type 805 and n-type 810 semiconducting (or "semiconductor") materials, and electrically conducting material 815 connecting pairs of n-type and p-type semiconductors. The Peltier heating device 801 may include a layer of a thermally insulating material over the n-type and p-type semiconductors. The layer of thermally insulating material may be a ceramic material. The Peltier heating device 801 may provide heating or cooling to the microplate 800, including wells (or chambers) of the microplate 800. In some cases, the microplate 800 may be heated with the aid of the Peltier heating device 801 in addition to passing a current through the microplate 800, as described above.

As another alternative, the microplate of FIG. 1 may be contacted on an underside of the microplate (e.g., adjacent to the metal plate of the microplate) with a resistive, radiative or convective heating device for providing heating (or cooling) to one or more wells of the microplate. In some cases, the microplate of FIG. 1 may be contacted on the underside with a clamp heating device. The clamp heating device may be used in conjunction with heating supplied with the aid of current directed through the microplate, as described above.

In some cases, heating devices provided herein may be used for both heating and cooling. For instance, the Peltier heating devices of FIGS. 7 and 8 may be used for removing heat from one or more wells of a microplate by, for example, adjusting the direction of the flow of current through the semiconductor-containing elements of the Peltier heating devices. As another example, cooling may be provided by decreasing a heating rate of a heating device, thereby enabling cooling to a pseudo-steady state temperature with the aid of convective, conductive or radiative heat transfer.

Methods for Forming Microplates

Another aspect of the present disclosure provides methods for forming microplates. Microplates provided herein can include substrates having one or more metals. In some embodiments, such substrates can include aluminum, aluminum oxide, an aluminum-containing alloy or composite material. In some cases, such substrates include aluminum. Current may be provided to substrates through electrodes in electrical contact with the substrates. In some cases, low or substantially low resistance electrical contacts may be provided to aluminum substrates for providing current to and through the aluminum substrates.

In some cases, aluminum substrates may be in electrical communication with electrical contacts (or electrodes) at a junction resistance less than or equal to about 5 m-ohms, or 10 m-ohms, or 15 m-ohms, or 20 m-ohms, or 25 m-ohms, or 30 m-ohms, or 35 m-ohms, or 40 m-ohms, wherein 1 m-ohm is equal to $1\times10^{-6}$ ohms. Such electrical contacts may have a low concentration of an aluminum-containing oxide, such as aluminum oxide, $AlO_x$, wherein 'x' is a number greater than zero.

In some cases, upon manufacturing a microplate having an aluminum substrate, corrugations may be pressed of formed in areas of the aluminum substrate for providing electrical contacts to the substrates. For instance, if six electrical contact areas are desired, each of the six electrical contact areas may corrugated prior to forming the electrical contact areas. Such corrugation may break any aluminum oxide that may be formed on a surface of the aluminum substrate, thereby providing for low or substantially low resistance electrical contacts to the aluminum substrate.

In some embodiments, one or more components of microplates are formed with the aid of a die or a plurality of dies. In some cases, microplates are formed by mechanical cold forming processing, such as forging (e.g., swaging). For instance, the metal plate of the microplate of FIG. 1 can be formed using mechanical cold forming processing. In cases in which the wells of a microplate are formed of a polymeric material, the wells can be formed using extrusion or injection molding.

PCR Systems

Another aspect of the present disclosure provides a system for sample processing, including heating for PCR. The system can include a controller with a central processing, memory (random-access memory and/or read-only memory), a data storage unit (e.g., hard drive), a communications port (COM PORTS), and an input/output (I/O) module, such as an I/O interface. The processor may be a central processing unit (CPU) or a plurality of CPU's for parallel processing. The memory and/or data storage unit can have machine-readable code for implementing the methods provided herein, such as heating methods for PCR.

Figure 9:
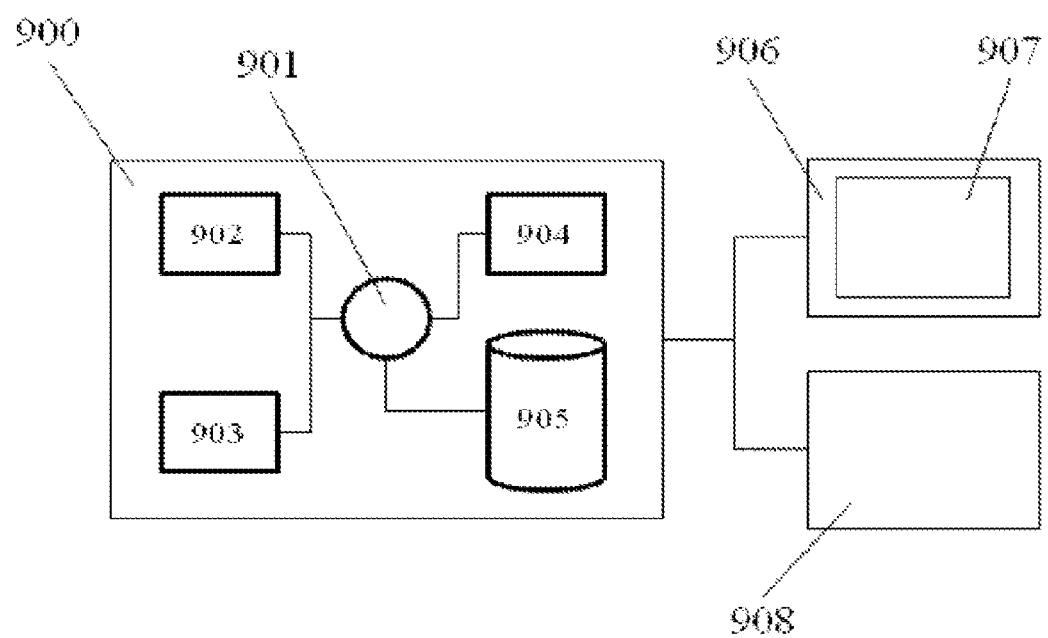
FIG. 9 shows a system for performing PCR, in accordance with an embodiment of the invention.

FIG. 9 shows a system 900 for regulating PCR using microplates provided herein, in accordance with an embodiment of the invention. The system 900 includes a processor 901, memory 902, input/output module 903, communications interface 904 and data storage unit 905. The system 900 can be operatively coupled to a display 906 for presenting a user interface 907 to a user operating the system 900. The user interface 907 in some cases is a graphical user interface (GUI) having one or more textual, graphical, audio and video elements. The display 906 can be a touch screen, such as a capacitive touch or resistive touch screen. In some embodiments, the display 906 is disposed adjacent to the system 900. In other embodiments, the display 906 is disposed remotely from the system 900.

The system 900 is operatively coupled to a PCR system 908 for performing PCR using microplates provided herein. The PCR system 908 can include sensors (e.g., thermocouples) for enabling the system 900 to make temperature measurements during PCR with the aid of the PCR system 908.

The memory 902 can be random-access memory (RAM) or read-only memory (ROM), to name a few examples, or a hard drive. The memory can include machine-readable code for implementing a method for performing PCR using the PCR system 908. In some embodiments, the memory 902 includes machine-readable code for executing one or more temperature profiles, which can include temperature zone profiles as a function of time.

In an example, a user inputs a PCR microplate having a sample into the PCR system 908. The PCR microplate can be as described herein. With the aid of the user interface 907 of the display, the user requests that the system 900 initiate sample processing and perform PCR on the sample. The system 900 executes code stored on the memory 902 to provide a programmed temperature profile (e.g., ramp rate) to the sample to conduct PCR.

The system 900 can be in wired or wireless communication with a remote system for housing data or providing instructions for PCR (see below). Communication to and from the system can be facilitated by a network interface that brings the system and in communication with the remote system through an intranet or the Internet (e.g., the World Wide Web).

Aspects of the systems and methods provided herein may be embodied in programming. Various aspects of the technology may be thought of as "products" or "articles of manufacture" typically in the form of executable code and/or associated data that is carried on or embodied in a type of machine-readable medium. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server or an intensity transform system. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Another aspect of the present disclosure provides a method for conducting PCR in which one or more of data from the reaction (e.g., fluorescence information, measured temperature), instructions for conducting PCR (e.g., ramp rate, predetermined temperature profile) and instructions for processing the data are located on a microplate, remotely or on a removable device. This can enable for plug-and-play PCR in which PCR can be performed across various platforms without the need for additional setup.

In some cases, a removable device can be configured to interface with systems for conducting PCR, such as the system 900 of FIG. 9. In an example, the removable device is a universal serial bus (USB) drive (e.g., USB stick), or a removable memory disk (e.g., flash drive). In another example, the removable disk is a compact flash disk, or device configured to communicate with a serial advanced technology attachment interface (e.g., mini SATA, or M-SATA) or a personal computer memory card international association (PCMCIA, also PC card) interface.

In some situations, both control and analysis instructions are provided on the removable device to allow a user to develop an experiment and analyze the results independently from a thermal cycler used for conducting the PCR reaction. Machine-readable instructions for implementing PCR can be located on the removable device. In some embodiments, the removable disk includes instructions and/or commands (e.g., as embodied in machine-readable code) that enable an identification of the type of hardware (or system, such as the system 900) interfacing with the removable device. The removable device can include processing instructions for performing PCR on the hardware. The processing instructions can be predetermined based on the type of system coupled to the removable device and/or the type of sample. The removable device can help identify the type of hardware it is plugged into and provide predetermined commands/interfaces to conduct PCR on that hardware directly without having to be installed on the hardware.

Some embodiments provide a removable device and software located on a removable device that is configured to operate on various platforms. Test system software houses both control and analysis programs so that the user can develop the user's experiment and understand the results. Whilst operating on the machine itself it is also desirable that it will operate remotely to enable experimental design and results analysis to occur away from the test system. This software can reside on a removable device, such as a USB stick, other removable memory disks, such as, for example, a compact flash, M-SATA, or PCMCIA device.

Such systems and devices provide various advantages. For example, having commands and/or instructions on a removable device can preclude the need for any additional installation. PCR can be conducted in such cases without the need for administrator privileges, and it be can performed on a machine without having to be installed on that machine. This provides a uniform platform for sample processing, as no hardware and/or software upgrades or installation may be required to setup a system (e.g., system 900) for PCR on a particular sample. The removable media can store both the data files and the program so as to enable compatibility.

PCR systems provided herein are configured for installation and operation on various software platforms, such as Windows-based (e.g., Windows 7) and Linux-based (e.g., Mac OS X) operating systems. Systems provided herein can be implemented on portable electronic devices, such as laptop computers, Smartphone (e.g., Apple iPhone®) and tablets (e.g., Apple iPad®). In some cases, such systems can communicate with peripheral devices for PCR, such as a heating system (e.g., current application device in communication with a microplate to define a circuit). This can provide for an interface for ready recognition across various platforms.

PCR systems provided herein can be platform independent. In some situations, as long as the system can accept the removable memory device, then it would be able to run the software and conduct PCR. In some cases, all the information is stored on the removable device such that nothing is held on the platform that is running the software, which may reduce, if not eliminate, data security issues. The data and the application are transferred from the removable device, and the system provides the computing power and associated ancillary functions, such as a user interface and printing.

Alternatively, PCR commands and/or instructions are stored a remote server (i.e., the "cloud") and accessed by the system (e.g., the system 900) through a network interface, such as a wired or wireless interface. A user can run PCR by providing a microplate, as described herein having a sample, and using the system to retrieve the requisite instructions for conducting PCR. Data gathered through the course of PCR can be stored on the system and subsequently uploaded to the remote server having a data storage unit.

Alternatively, PCR commands and/or instructions are stored on a memory device that is integrated in a microplate. The microplate is configured to interface with a system for conducting PCR, such as the system 900 of FIG. 9. The system can include a reader for recognizing the memory device and subsequently preparing the system for sample processing. In some embodiments, the memory device is an electrically erasable programmable read-only memory (EEPROM).

In some embodiments, a microplate (or sample holder) includes an identification member for enabling a system (e.g., the system 900 of FIG. 9) to identify the microplate. The identification member can be a solid state device, such as a processor (e.g., microprocessor) or memory, or a radio-frequency identification (RFID) tag or device. The identification member can be for identification and in some cases data storage. This can advantageously aid in reducing handling errors. In an example, a microplate includes an RFID device that stores both instructions (e.g., PCR instructions, data processing instructions) and identifying information. The identifying information can be a serial number. The identifying information can enable a system to identify the microplate. In some situations, the RFID device only includes identifying information, and a system, such as the system 900 of FIG. 9, is configured to detect the RFID and retrieve the identifying information, and to retrieve instructions for conducting PCR with the aid of the microplate. In some cases, the instructions retrieved by the system are specific to the microplate operatively coupled to the system.

User Interfaces

Another aspect of the present disclosure provides a user interface for enabling a user to setup a system for PCR, monitor PCR, and view PCR results. The user interface in some cases is a graphical user interface (GUI) having one or more textual, graphical, audio and video elements, such as menu elements for enabling a user to setup a PCR task, monitor the course of PCR, review results and conduct data analysis. The GUI can facilitate the implementation of PCR experiments. FIGS. 11-17 illustrate screenshots of a GUI that allows ready analysis and visualization of PCR results, as described herein. The GUI of FIGS. 11-17 can be implemented on systems provided herein, such as the system 900 of FIG. 9, and presented to a user with the aid of a display, such as the display 906 of FIG. 9.

Figure 11:
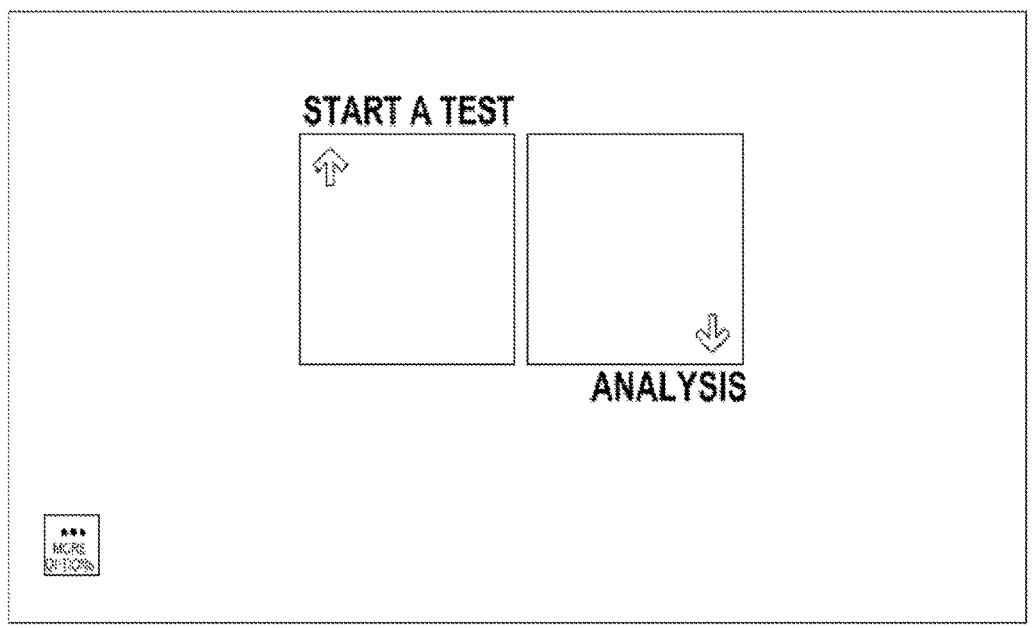
FIGS. 11-17 illustrate exemplary screenshots of a graphical user interface, in accordance with an embodiment of the invention.

FIG. 11 shows a GUI having various menu options, including "START A TEST" and "ANALYSIS." A user can select the START A TEST option to initiate PCR of a sample in a microplate coupled to a system having the GUI. The user can select ANALYSIS to analyze PCR data. The menu options can be selected with the aid of a pointing device, such as a mouse or the user's finger in cases in which the GUI is displayed on a touch screen.

Figure 12:
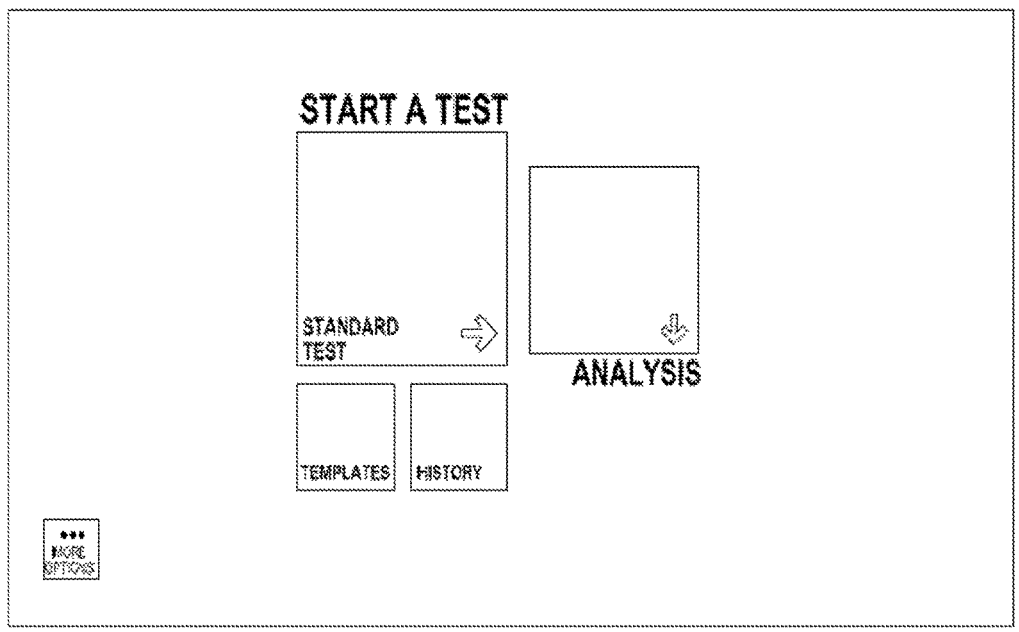

In FIG. 12, the user has selected START A TEST and the system presents the user with sub-menu options, including TEMPLATES and HISTORY. The user can select TEMPLATES to access various test templates for performing PCR. Alternatively, the user can select HISTORY to review, for example, PCR history, such as what tests were conducted at a particular point in time. Such data can be stored in a data repository of the system. The user can select STANDARD TEST to proceed with setting up the system to conduct PCR.

Figure 13:
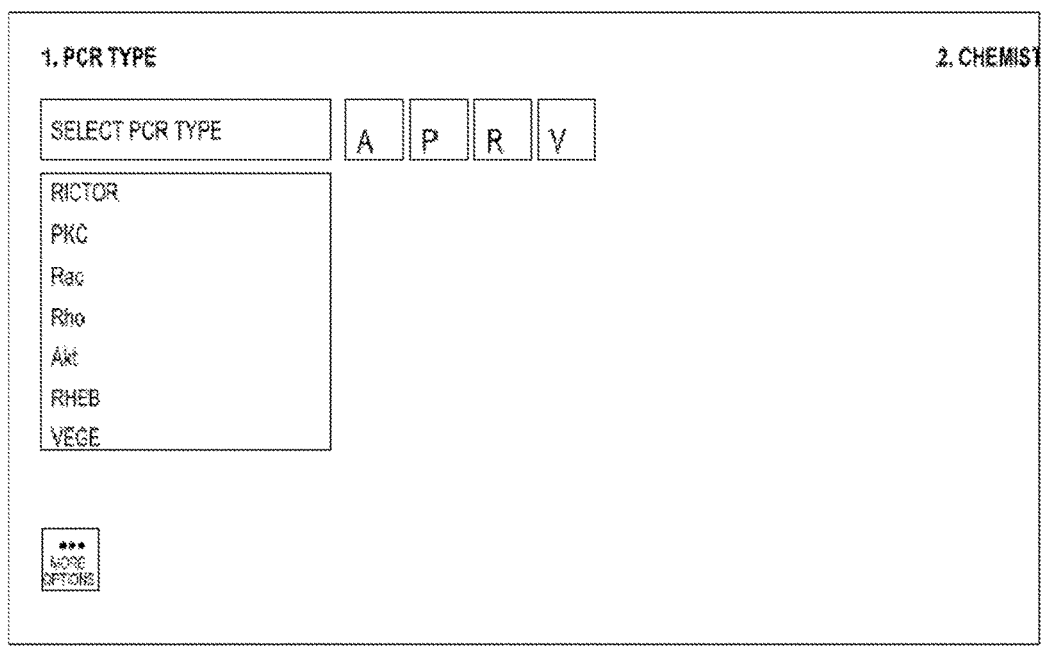
Figure 14:
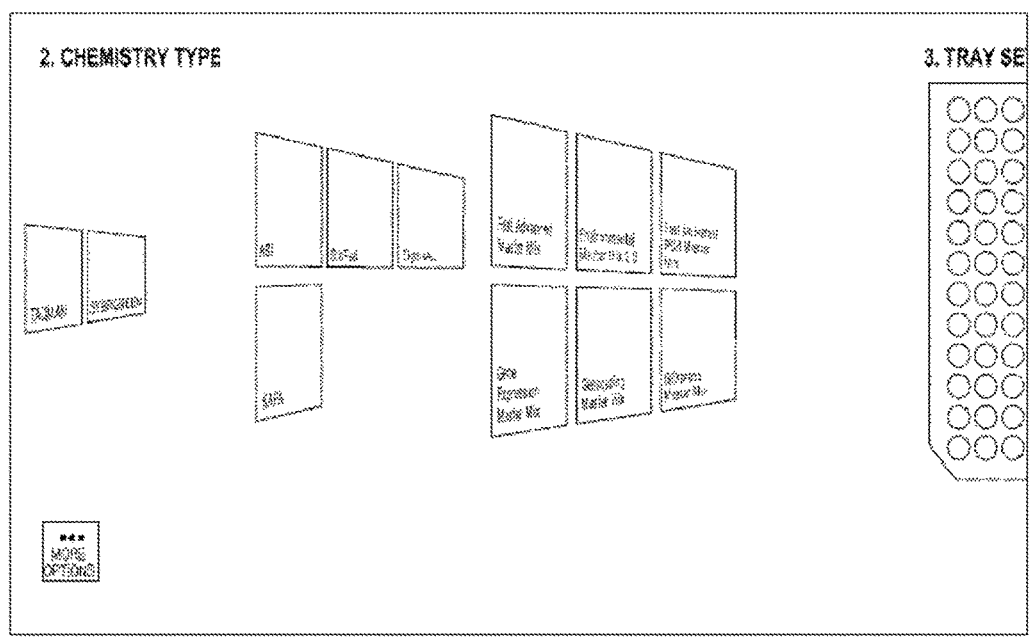
Figure 15:
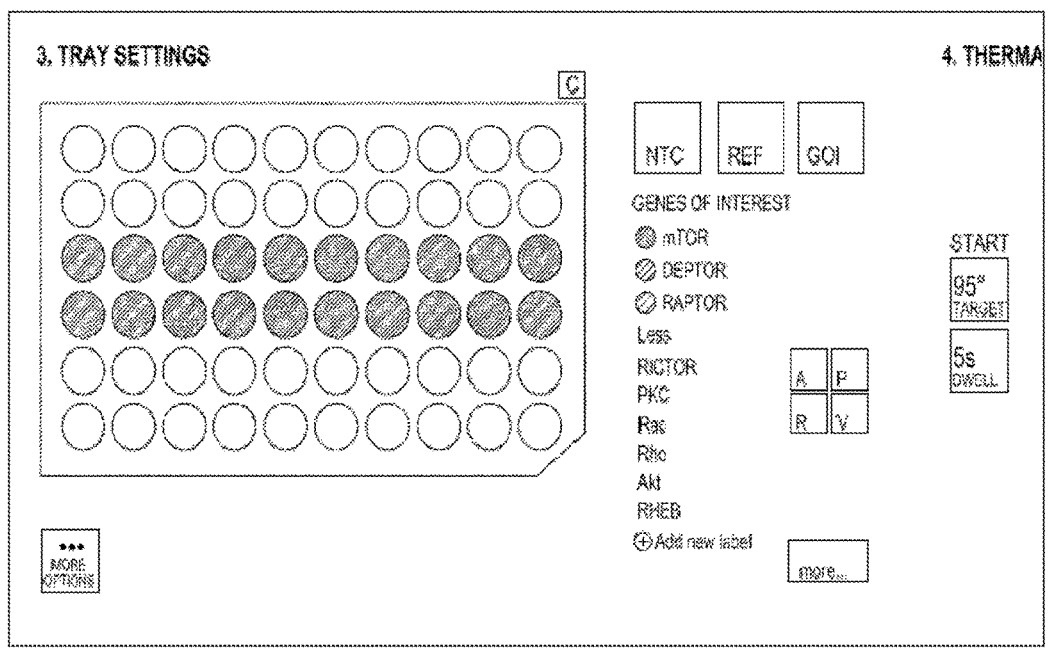
Figure 16:
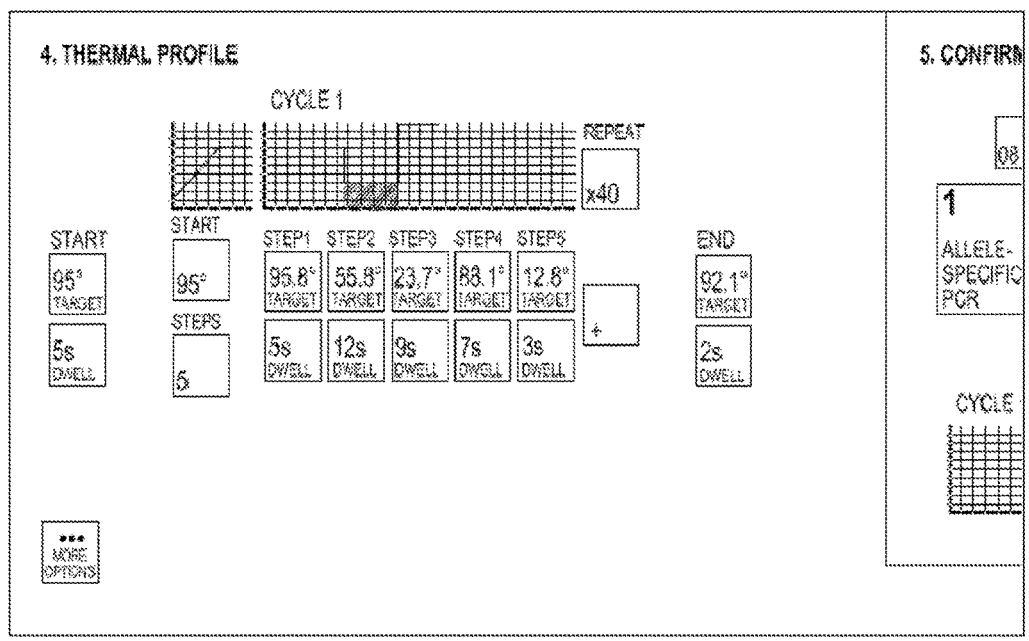
Figure 17:
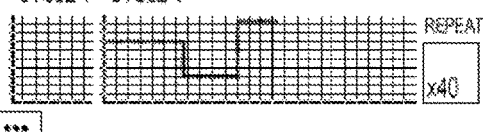

With reference to FIG. 13, under STANDARD TEST, the system presents the user with various PCR options, such requesting that the user select the type of PCR ("SELECT PCR TYPE"). The system presents the user with various PCR type options, including RICTOR, PKC, Rac, Rho, Akt and RHEB. The user can select a PCR type option. Next, with reference to FIG. 14, the system presents the user with various chemistry types ("CHEMISTRY TYPE"), such as ABI, Fast Advanced Master Mix and Gene Expression Master Mix. Next, with reference to FIG. 15, the system presents the user with tray settings ("TRAY SETTINGS") and enables the user to select genes of interest ("GENES OF INTEREST"), such as mTOR or RAPTOR. Next, with reference to FIG. 16, the system presents the user with thermal profile options, including start temperatures and target temperatures. The user can select from predetermined options, or manually input temperature settings. The system then presents the user with a confirmation screen, as shown in FIG. 17. The confirmation screen shows a temperature profile per cycle that the system will use in the PCR, the number of cycles ("REPEAT"), tray settings ("24 WELLS" has been selected in FIG. 17), among other settings. The temperature profile is a custom temperature profile, though predetermined settings may be used, if desired. The system provides the user the option to change the settings, or to proceed with conducting PCR ("RUN TEST").

Example 1: Coated Metal Plate

Nominally 0.4 mm thick metal plates were produced from bulk processed material on a large scale where a metal ingot (e.g., 5 ton metal ingot) enters the process and is rolled and coated in a continuous operation. The material was an aluminum alloy rolled to a half-hard condition and then coated on one side (e.g., a top side) to a nominal thickness of about 10 microns with a polypropylene compatible material. This material allows polypropylene to be heat-sealed (or welded) to the metal plate, and does not inhibit the PCR. The other side (bottom) of the sheet was coated with an epoxy primer to a nominal thickness of 5 microns. This is present to normalize the infrared emissivity of the bottom side of the sheet. The material was slit into 160 mm wide strips and supplied in coiled form to an automatic stamping line where the individual plates are produced. The epoxy coating was then selectively removed from the contact fingers at the ends of the plates to allow electrical contact to be made.

Example 2: Polypropylene Moulding

To contain the liquid samples placed on the plate, a polypropylene moulding consisting of an array of vertical tube structures was welded to the metal plate of Example 1. The polypropylene moulding was formed of a plurality of tubes to define sample areas (or wells). The size and pattern of the tubes may be a matter of user choice; any pattern that fits within the actively temperature-controlled area in the middle of the plate may be used. Two familiar-looking options were selected: a 6×4 tube array on a 9 mm pitch, and an 8×12 array on a 4.5 mm pitch. The whole assembly weighed 10.5 g and was readily recyclable. Appropriately for a single-use item, the manufacturing cost of the consumable was low.

While certain microplates have been described as being consumable ore recyclable, it will be appreciated that in some cases such microplates need not be consumable or recyclable. In some embodiments, such microplates may be reusable, non-consumable, or non-recyclable.

Microplates of the present disclosure may be suited for use in nucleic acid amplification, including, without limitation, polymerase chain reaction (PCR) and transcription mediated amplification. Thus, while certain microplates have been described in the context of PCR, it will be understood that microplates of the present disclosure may be used to implement other types of nucleic acid amplification.

Systems and methods provided herein may be combined with or modified by other systems and methods. For example, systems and methods provided herein may be combined with or modified by systems and methods described in U.S. Pat. No. 6,635,492 to Gunter ("Heating specimen carriers") and U.S. Pat. No. 6,949,725 to Gunter ("Zone heating of specimen carriers"), and PCT Publication Nos. WO/2001/072424 to Gunter ("Heating specimen carriers"), WO/1997/026993 to Gunter ("Heating"), WO/2005/058501 to Gunter ("Heating samples in specimen carriers"), WO/2003/022439 to Gunter ("Zone heating of specimen carriers"), WO/2012/080746 to Gunter et al. ("METHODS AND SYSTEMS FOR FAST PCR HEATING") and U.S. Patent Publication No. 2012/0214207 to Gunter et al. ("METHODS AND SYSTEMS FOR FAST PCR HEATING"), which patents and patent publications are entirely incorporated herein by reference.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method for forming a low resistance electrical connection between a microplate and a busbar in a thermocycler, comprising:
    (a) providing a clamp comprising a spring-loaded pivot coupled to a ram; and
    (b) using the spring-loaded pivot to provide linear motion to the ram to press the microplate against the bus-bar.

2. The method of claim 1, wherein the clamp is an over center toggle type clamp.

3. The method of claim 1, wherein the clamp provides control over a force applied by the ram over a range of adjustments.

4. The method of claim 1, wherein the clamp is closed by hand to form the low resistance electrical connection between the microplate and the bus-bar.

5. The method of claim 1, wherein the clamp is capable of exerting a force of between about 1,500 and 2,000 Newtons to the microplate and/or the bus-bar.

6. The method of claim 1, wherein the clamp deforms the microplate, thereby disrupting an oxide film on a surface of the microplate.

7. The method of claim 1, wherein the low resistance electrical resistance at an interface between the microplate and the bus-bar is less than a resistance of the microplate.

8. The method of claim 1, wherein the microplate is consumable.

9. The method of claim 1, wherein the microplate comprises:
    (a) a substrate comprising a metallic material for heating a sample during polymerase chain reaction (PCR);
    (b) a barrier layer disposed adjacent to the substrate, the barrier layer formed of a first polymeric material; and
    (c) one or more wells for holding the sample during PCR, the one or more wells formed of a second polymeric material sealed to the barrier layer,
    wherein the substrate provides a PCR ramp rate of at least 5° C./second.

10. The method of claim 9, wherein the microplate heats the sample upon flow of electric current through the substrate.

11. The method of claim 9, wherein the metallic material has a resistivity between about $2\times10^{-8}$ ohm-m and $8\times10^{-8}$ ohm-m.

12. The method of claim 9, wherein the metallic material comprises aluminum.

13. The method of claim 9, wherein the microplate has a thickness of less than 1 mm.

14. The method of claim 9, wherein the substrate increases a temperature of the sample at a rate between about 5° C./s and about 15° C./s.

15. The method of claim 9, wherein the one or more wells comprise at least 24 wells.

16. The method of claim 9, wherein the one or more wells comprise at least 96 wells.

17. The method of claim 9, wherein the substrate provides well-to-well thermal uniformity of at least about +/−0.5° C. without an external heating element or a Peltier heating block.

18. The method of claim 9, wherein the substrate provides a heating efficiency sufficient for at least about 2 PCR cycles per minute, including fluorescence measurements for every cycle.

19. The method of claim 9, wherein the barrier layer has a thickness of less than 10 micrometers.

20. The method of claim 1, further comprising (c) providing a sample in the microplate and (d) using the microplate to heat the sample at a rate of at least about 10° C./second.

* * * * *